(12) United States Patent
Hale et al.

(10) Patent No.: US 7,659,294 B2
(45) Date of Patent: Feb. 9, 2010

(54) 2-(ARYL)AZACYCLYLMETHYL CARBOXYLATES, SULFONATES, PHOSPHONATES, PHOSPHINATES AND HETEROCYCLES AS S1P RECEPTOR AGONISTS

(75) Inventors: Jeffrey John Hale, Westfield, NJ (US); Lin Yan, East Brunswick, NJ (US)

(73) Assignee: Merck & Co., Inc., Rahway, NJ (US)

( * ) Notice: Subject to any disclaimer, the term of this patent is extended or adjusted under 35 U.S.C. 154(b) by 408 days.

(21) Appl. No.: 11/665,046

(22) PCT Filed: Oct. 18, 2005

(86) PCT No.: PCT/US2005/037652

§ 371 (c)(1),
(2), (4) Date: Apr. 9, 2007

(87) PCT Pub. No.: WO2006/047195

PCT Pub. Date: May 4, 2006

(65) Prior Publication Data

US 2009/0042954 A1    Feb. 12, 2009

Related U.S. Application Data

(60) Provisional application No. 60/621,313, filed on Oct. 22, 2004.

(51) Int. Cl.
  A61K 31/4245  (2006.01)
  C07D 271/10   (2006.01)
  C07D 413/10   (2006.01)

(52) U.S. Cl. .................. 514/364; 548/125; 548/131; 548/240; 548/251; 548/255; 546/268.1; 546/268.4; 546/269.4; 544/224; 544/242; 544/336; 514/361; 514/378; 514/381; 514/385

(58) Field of Classification Search .................. 548/125, 548/131, 136, 240, 250, 251, 255, 300.1, 548/356.1; 546/268.1, 268.4, 269.4; 544/224, 544/242, 336; 514/361, 364, 378, 381, 385
See application file for complete search history.

(56) References Cited

U.S. PATENT DOCUMENTS 6,720,343 B2    4/2004    Yoshioka et al.

*Primary Examiner*—Golam M Shameem
(74) *Attorney, Agent, or Firm*—Yong Zhao; Valerie J. Camara

(57) ABSTRACT

The present invention encompasses compounds of Formula I:

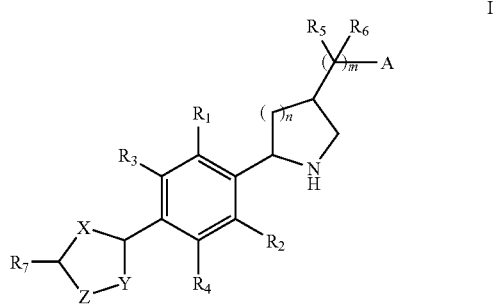

as well as the pharmaceutically acceptable salts thereof. The compounds are $S1P_1$/Edg1 receptor agonists and thus have immunosuppressive, anti-inflammatory and hemostatic activities by modulating leukocyte trafficking, sequestering lymphocytes in secondary lymphoid tissues, and enhancing vascular integrity. The invention is also directed to pharmaceutical compositions containing such compounds and methods of treatment or prevention.

11 Claims, No Drawings

US 7,659,294 B2

2-(ARYL)AZACYCLYLMETHYL CARBOXYLATES, SULFONATES, PHOSPHONATES, PHOSPHINATES AND HETEROCYCLES AS S1P RECEPTOR AGONISTS

CROSS REFERENCE TO RELATED APPLICATIONS

This application is a U.S. national Phase application under 35.U.S.C. §371 of PCT Application No. PCT/CA2005/037652, filed Oct. 18, 2005, which claims priority under 35 U.S.C. 119 to U.S. No. 60/621,313, filed Oct. 22, 2004.

BACKGROUND OF THE INVENTION

The present invention is related to compounds that are $S1P_1$/Edg1 receptor agonists and thus have immunosuppressive, anti-inflammatory and hemostatic activities by modulating leukocyte trafficking, sequestering lymphocytes in secondary lymphoid tissues, and enhancing vascular integrity. The invention is also directed to pharmaceutical compositions containing such compounds and methods of treatment or prevention.

Immunosuppressive and antiinflammatory agents have been shown to be useful in a wide variety of autoimmune and chronic inflammatory diseases, including systemic lupus erythematosis, chronic rheumatoid arthritis, type I diabetes mellitus, inflammatory bowel disease, biliary cirrhosis, uveitis, multiple sclerosis and other disorders such as Crohn's disease, ulcerative colitis, bullous pemphigoid, sarcoidosis, psoriasis, autoimmune myositis, Wegener's granulomatosis, ichthyosis, Graves opthalmopathy, atopic dermatitis and asthma, chronic pulmonary disease, acute lung injury, acute respiratory distress syndrome, and sepsis. They have also proved useful as part of chemotherapeutic regimens for the treatment of cancers, lymphomas and leukemias.

Although the underlying pathogenesis of each of these conditions may be quite different, they have in common the activation of the immune system and the appearance of a variety of autoantibodies, self-reactive lymphocytes and/or activation of cells involved in innate immunity. Such self-reactivity may be due, in part, to a loss of the homeostatic controls under which the normal immune system operates. Similarly, following a bone-marrow or an organ transplantation, the host lymphocytes recognize the foreign tissue antigens and begin to produce both cellular and humoral responses including antibodies, cytokines and cytotoxic lymphocytes which lead to graft rejection.

One end result of an autoimmune or a rejection process is increased vascular permeability and tissue destruction caused by inflammatory cells and the mediators they release. Anti-inflammatory agents such as NSAIDs act principally by blocking the effect or secretion of these mediators but do nothing to modify the immunologic basis of the disease. On the other hand, cytotoxic agents, such as cyclophosphamide, act in such a nonspecific fashion that both the normal and autoimmune responses are shut off. Indeed, patients treated with such nonspecific immunosuppressive agents are as likely to succumb to infection as they are to their autoimmune disease.

Cyclosporin A is a drug used to prevent rejection of transplanted organs. FK-506 is another drug approved for the prevention of transplant organ rejection, and in particular, liver transplantation. Cyclosporin A and FK-506 act by inhibiting the body's immune system from mobilizing its vast arsenal of natural protecting agents to reject the transplant's foreign protein. Cyclosporin A was approved for the treatment of severe psoriasis and has been approved by European regulatory agencies for the treatment of atopic dermatitis.

Though they are effective in delaying or suppressing transplant rejection, Cyclosporin A and FK-506 are known to cause several undesirable side effects including nephrotoxicity, neurotoxicity, and gastrointestinal discomfort. Therefore, an immunosuppressant without these side effects still remains to be developed and would be highly desirable.

The immunosuppressive compound FTY720 is a lymphocyte sequestration agent currently in clinical trials. FTY720 is metabolized in mammals to a compound that is a potent agonist of sphingosine 1-phosphate receptors. Agonism of sphingosine 1-phosphate receptors modulates leukocyte trafficking, induces the sequestration of lymphocytes (T-cells and B-cells) in lymph nodes and Peyer's patches without lymphodepletion, and disrupts splenic architecture, thereby interfering with T cell dependent antibody responses. SIP receptor agonists also have anti-inflammatory properties by enhancing endothelial integrity and inhibiting vascular damage consequent to the activation of the immune system. Such immunosuppression and antiinflammation is desirable to prevent rejection after organ transplantation, in the treatment of autoimmune disorders, and in the treatment of conditions that have an underlying defect in vascular integrity, such as acute lung injury, acute respiratory distress syndrome, and sepsis,—see Groeneveld, A. B. J. 2003. Vascular Pharm. 39:247-256.

Sphingosine 1-phosphate is a bioactive sphingolipid metabolite that is secreted by hematopoietic cells and stored and released from activated platelets. Yatomi, Y., T. Ohmori, G. Rile, F. Kazama, H. Okamoto, T. Sano, K. Satoh, S. Kume, G. Tigyi, Y. Igarashi, and Y. Ozaki. 2000. *Blood.* 96:3431-8. It acts as an agonist on a family of G protein-coupled receptors to regulate cell proliferation, differentiation, survival, and motility. Fukushima, N., I. Ishii, J. J. A. Contos, J. A. Weiner, and J. Chun. 2001. Lysophospholipid receptors. Annu. Rev. Pharmacol. Toxicol. 41:507-34; Hla, T., M.-J. Lee, N. Ancellin, J. H. Paik, and M. J. Kluk. 2001. Lysophospholipids—Receptor revelations. *Science.* 294:1875-1878; Spiegel, S., and S. Milstien. 2000. Functions of a new family of sphingosine-1-phosphate receptors. *Biochim. Biophys. Acta.* 1484:107-16; Pyne, S., and N. Pyne. 2000. Sphingosine 1-phosphate signalling via the endothelial differentiation gene family of G-protein coupled receptors. *Pharm. & Therapeutics.* 88:115-131. Five sphingosine 1-phosphate receptors have been identified ($S1P_1$, $S1P_2$, $S1P_3$, $S1P_4$, and $S1P_5$, also known as endothelial differentiation genes Edg1, Edg5, Edg3, Edg6, Edg8), that have widespread cellular and tissue distribution and are well conserved in human and rodent species (see Table). Binding to SIP receptors elicits signal transduction through Gq-, Gi/o, G12-, G13-, and Rho-dependent pathways. Ligand-induced activation of $S1P_1$ and $S1P_3$ has been shown to promote angiogenesis, chemotaxis, and adherens junction assembly through Rac- and Rho-, see Lee, M.-J., S. Thangada, K. P. Claffey, N. Ancellin, C. H. Liu, M. Kluk, M. Volpi, R. I. Sha'afi, and T. Hla. 1999. *Cell.* 99:301-12. SIP enhances endothelial barrier integrity by assembling cortical actin cytoskeletal structures and strengthening cell:cell junctions and cell:extracellular matrix interactions through SIP receptors, primarily S1P1—, see Garcia, J. G. N, F. Liu, A. D. Verin, A. Birukova, M. A. Dechert, W. T. Gerthoffer, J. R. Bamburg, D. English, 2001. J. Clin. Invest. 108:689-701, and SiP receptor agonists, including FTY720, can inhibit vascular permeability induced by VEGF in mice, see Sanchez, T., T. Estrada-Hernandez, J.-H. Paik, M.-T. Wu, K. Venkataraman, V. Brinkmann, K. Claffey, and T. Hla. 2003. *J. Biol. Chem.* 278:47281-47290.

Administration of sphingosine 1-phosphate to animals induces systemic sequestration of peripheral blood lymphocytes into secondary lymphoid organs, thus resulting in therapeutically useful immunosuppression, see Mandala, S., R. Hajdu, J. Bergstrom, E. Quackenbush, J. Xie, J. Milligan, R. Thornton, G.-J. Shei, D. Card, C. Keohane, M. Rosenbach, J. Hale, C. L. Lynch, K. Rupprecht, W. Parsons, H. Rosen. 2002. *Science.* 296:346-349. However, sphingosine 1-phosphate also has cardiovascular and bronchoconstrictor effects that limit its utility as a therapeutic agent. Intravenous administration of sphingosine 1-phosphate decreases the heart rate, ventricular contraction and blood pressure in rats, see Sugiyama, A., N, N. Aye, Y. Yatomi, Y. Ozaki, and K. Hashimoto. 2000. *Jpn. J. Pharmacol.* 82:338-342. In human airway smooth muscle cells, sphingosine 1-phosphate modulates contraction, cell growth and cytokine production that promote bronchoconstriction, airway inflammation and remodeling in asthma, see Ammit, A. J., A. T. Hastie, L. C. Edsall, R. K. Hoffman, Y. Amrani, V. P. Krymskaya, S. A. Kane, S. P. Peters, R. B. Penn, S. Spiegel, R. A. Panettieri. Jr. 2001, *FASEB J* 15:1212-1214. The undesirable effects of sphingosine 1-phosphate are associated with its non-selective, potent agonist activity on all S1P receptors.

The present invention encompasses compounds which are agonists of the $S1P_1/Edg1$ receptor having selectivity over the $S1P_3/Edg3$ receptor. An $S1P_1/Edg1$ receptor selective agonist has advantages over current therapies and extends the therapeutic window of lymphocyte sequestration and vascular integrity agents, allowing better tolerability with higher dosing and thus improving efficacy as monotherapy.

While the main use for immunosuppressants and antiinflammatory agents is in treating bone marrow, organ and transplant rejection, other uses for such compounds include the treatment of arthritis, in particular, rheumatoid arthritis, insulin and non-insulin dependent diabetes, multiple sclerosis, psoriasis, inflammatory bowel disease, Crohn's disease, lupus erythematosis, asthma, allergies, chronic pulmonary disease, acute lung injury, acute respiratory disease syndrome, sepsis and the like.

Thus, the present invention is focused on providing immunosuppressant and vascular integrity compounds that are safer and more effective than prior compounds. These and other objects will be apparent to those of ordinary skill in the art from the description contained herein.

Summary of SIP Receptors

| Name | Synonyms | Coupled G proteins | mRNA expression |
|---|---|---|---|
| $S1P_1$ | Edg1, $LP_{B1}$ | $G_{i/o}$ | Widely distributed, endothelial cells |
| $S1P_2$ | Edg5, $LP_{B2}$, AGR16, H218 | $G_{i/o}, G_q,$ $G_{12/13}$ | Widely distributed, vascular smooth muscle cells |
| $S1P_3$ | Edg3, $LP_{B3}$ | $G_{i/o}, G_q,$ $G_{12/13}$ | Widely distributed, endothelial cells |
| $S1P_4$ | Edg6, $LP_{C1}$ | $G_{i/o}$ | Lymphoid tissues, lymphocytic cell lines |
| $S1P_5$ | Edg8, $LP_{B4}$, NRG1 | $G_{i/o}$ | Brain, spleen |

SUMMARY OF THE INVENTION

The present invention encompasses compounds of Formula I:

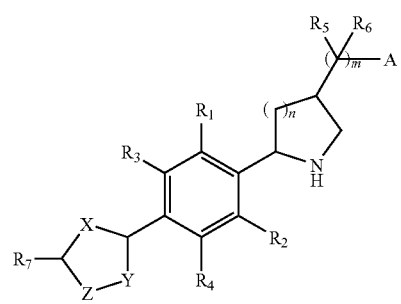

as well as the pharmaceutically acceptable salts thereof. The compounds are $S1P_1/Edg1$ receptor agonists and thus have immunosuppressive, anti-inflammatory and hemostatic activities by modulating leukocyte trafficking, sequestering lymphocytes in secondary lymphoid tissues, and enhancing vascular integrity. The invention is also directed to pharmaceutical compositions containing such compounds and methods of treatment or prevention.

DETAILED DESCRIPTION OF THE INVENTION

The invention encompasses a compound represented by Formula I

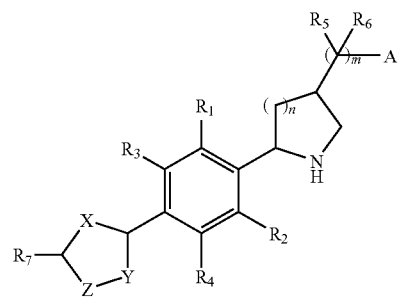

or a pharmaceutically acceptable salt thereof, wherein:

n is 0, 1, or 2;

m is 0, 1, or 2, such that when m is 0 then A is bonded directly to the azetidine (n=0), pyrrolidine (n=1), or piperidine (n=2) group shown in Formula I;

$R^1, R^2, R^3$, and $R^4$ are independently selected from the group consisting of: —H, —F, $C_1$-$C_4$alkyl, $C_1$-$C_4$ perfluoroalkyl, —Cl, —Br, $C_1$-$C_8$alkoxy, and —OCF$_3$;

$R^5$ and $R^6$ are independently selected from: —H, —OH, —F, $C_1$-$C_4$ alkyl, and $C_1$-$C_4$ perfluoroalkyl;

$R^7$ is selected from the group consisting of: phenyl, pyridinyl, pyrimidinyl, pyrazinyl, pyridizinyl and thienyl, each optionally substituted with one to three substituents independently selected from the group consisting of: —F, —Cl, —Br, —I, —CN, —OH, —NR$^8$R$^9$, —NO$_2$, phenyl, $C_1$-$C_6$alkyl, $C_3$-$C_6$cycloalkyl, $C_2$-$C_6$alkenyl, $C_2$-$C_6$alkynyl, $C_1$-$C_6$alkoxy, $C_3$-$C_6$cycloalkoxy, $C_1$-$C_6$alkylthio and $C_2$-$C_6$acyloxy, wherein said phenyl, $C_1$-$C_6$alkyl, $C_3$-$C_6$cycloalkyl, $C_2$-$C_6$alkenyl, $C_2$-$C_6$alkynyl, $C_1$-$C_6$alkoxy, $C_3$-$C_6$cycloalkoxy, $C_1$-$C_6$alkylthio and $C_1$-$C_6$acyloxy are each optionally substituted with one to three substituents independently selected from the group consisting of: —F, —Cl, —Br, —I, —OH and $C_1$-$C_5$alkoxy;

$R^8$ and $R^9$ are independently selected from the group consisting of: $C_1$-$C_6$ alkyl, $C_1$-$C_6$ alkenyl and $C_1$-$C_6$ alkynyl, each optionally substituted with one to three substituents independently selected from the group consisting of: —F, —Cl, —Br, —I, —OH and $C_1$-$C_5$alkoxy, or $R^8$ and $R^9$ may be joined together with the nitrogen atom to which they are attached to form a saturated monocyclic ring of 3 to 8 atoms, optionally containing 1 or 2 oxygen atoms, said ring is optionally substituted with one to three substituents independently selected from the group consisting of: —F, —Cl, —Br, —I, —OH and $C_{1-5}$alkoxy;

X, Y, and Z are independently selected from the group consisting of: —C=, —CH—, —O—, —N=, —NH—, —N($R^{10}$)— and —S— such that the resulting ring is an aromatic heterocycle;

$R^{10}$ is selected from the group consisting of: $C_1$-$C_6$ alkyl, $C_1$-$C_6$ alkenyl and $C_1$-$C_6$ alkynyl, each optionally substituted with one to three substituents independently selected from the group consisting of: —F, —Cl, —Br, —I, —OH and $C_1$-$C_5$alkoxy;

A is selected from the group consisting of: —$CO_2H$, —$PO_3H_2$, —$PO_2H_2$, —$SO_3H$, —$CONHSO_2R^{11}$, —$PO(R^{11})$OH,

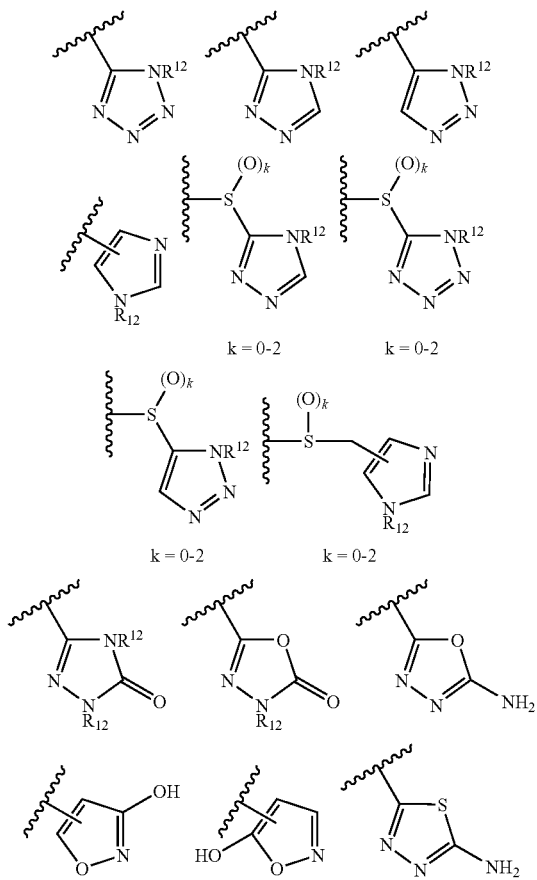

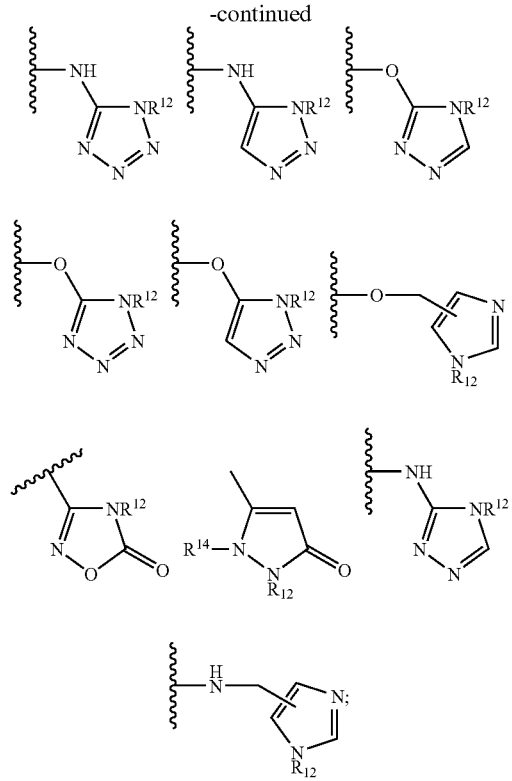

$R^{11}$ is selected from the group consisting of: $C_1$-$C_4$ alkyl, phenyl, —$CH_2OH$ and $CH(OH)$-phenyl, and each $R^{12}$ is independently selected from the group consisting of: —H and —$CH_3$.

An embodiment of the invention encompasses a compound of Formula I wherein A is —$CO_2H$.

Another embodiment of the invention encompasses a compound of Formula I wherein n is 1.

Another embodiment of the invention encompasses a compound of Formula I wherein m is 1.

Another embodiment of the invention encompasses a compound of Formula I wherein X is —N=, Y is —N= and Z is —O— such that the resulting ring formed is 1,2,4-oxadiazole.

Another embodiment of the invention encompasses a compound of Formula I wherein $R^7$ is phenyl, optionally substituted with one to three substituents independently selected from the group consisting of: —F, —Cl, —Br, —I, —CN, —OH, —$NR^7R^8$, —$NO_2$, phenyl, $C_1$-$C_6$alkyl, $C_3$-$C_6$cycloalkyl, $C_2$-$C_6$alkenyl, $C_2$-$C_6$alkynyl, $C_1$-$C_6$alkoxy, $C_3$-$C_6$cycloalkoxy, $C_1$-$C_6$alkylthio and $C_2$-$C_6$acyloxy, wherein said phenyl, $C_1$-$C_6$alkyl, $C_3$-$C_6$cycloalkyl, $C_2$-$C_6$alkenyl, $C_2$-$C_6$alkynyl, $C_1$-$C_6$alkoxy, $C_3$-$C_6$cycloalkoxy, $C_1$-$C_6$alkylthio and $C_1$-$C_6$acyloxy are each optionally substituted with one to three substituents independently selected from the group consisting of: —F, —Cl, —Br, —I, —OH and $C_1$-$C_5$alkoxy.

Another embodiment of the invention encompasses a compound represented by Formula Ia

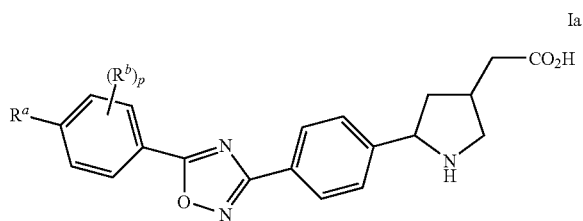

Ia or a pharmaceutically acceptable salt thereof, wherein:

p is 0, 1 or 2;

$R^a$ is selected from the group consisting of: phenyl, $C_1$-$C_6$alkyl, $C_3$-$C_6$cycloalkyl, $C_1$-$C_6$ alkoxy and $C_3$-$C_6$cycloalkoxy, wherein said phenyl $C_1$-$C_6$alkyl, $C_3$-$C_6$cycloalkyl, $C_1$-$C_6$alkoxy and $C_3$-$C_6$cycloalkoxy are each optionally substituted with one to three substituents independently selected from the group consisting of: —F, —Cl, —Br, —I and —OH; and $R^b$ is selected from the group consisting of: —F, —Cl, —Br, —I, —CN, —$CH_3$, —$OCH_3$, —$CF_3$, ethynyl, —$NO_2$ and —$NH_2$.

Another embodiment of the invention encompasses a compound of Formula Ia wherein p is 0 or 1, and $R^b$ is selected from the group consisting of: —F, —Cl and —$CF_3$.

Another embodiment of the invention encompasses a compound of Formula Ia wherein $R^a$ is selected from the group consisting of: $C_3$-$C_5$alkyl, cyclopentyl, cyclohexyl, $C_2$-$C_4$alkoxy, cyclopentyloxy and cyclohexyloxy, each optionally substituted with one to three fluoro groups.

The invention is further exemplified in the examples that follow.

The invention also encompasses a method of treating an immunoregulatory abnormality in a mammalian patient in need of such treatment comprising administering to said patient a compound of Formula I in an amount that is effective for treating said immunoregulatory abnormality.

Within this embodiment is encompassed the above method wherein the immunoregulatory abnormality is an autoimmune or chronic inflammatory disease selected from the group consisting of: systemic lupus erythematosis, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves opthalmopathy and asthma.

Also within this embodiment is encompassed the above method wherein the immunoregulatory abnormality is bone marrow or organ transplant rejection or graft-versus-host disease.

Also within this embodiment is encompassed the above method wherein the immunoregulatory abnormality is selected from the group consisting of: transplantation of organs or tissue, graft-versus-host diseases brought about by transplantation, autoimmune syndromes including rheumatoid arthritis, systemic lupus erythematosus, Hashimoto's thyroiditis, multiple sclerosis, myasthenia gravis, type I diabetes, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia greata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyperresponsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-$C_4$ release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, trauma, and chronic bacterial infection.

Also within this embodiment is encompassed the above method wherein the immunoregulatory abnormality is selected from the group consisting of:

1) multiple sclerosis,
2) rheumatoid arthritis,
3) systemic lupus erythematosus,
4) psoriasis,
5) rejection of transplanted organ or tissue,
6) inflammatory bowel disease, 7) a malignancy of lymphoid origin, 8) acute and chronic lymphocytic leukemias and lymphomas and 9) insulin and non-insulin dependent diabetes.

The invention also encompasses a method of suppressing the immune system in a mammalian patient in need of immunosuppression comprising administering to said patient an immunosuppressing effective amount of a compound of Formula I.

The invention also encompasses a pharmaceutical composition comprised of a compound of Formula I in combination with a pharmaceutically acceptable carrier.

The invention also encompasses a method of treating a respiratory disease or condition in a mammalian patient in need of such treatment comprising administering to said patient a compound of Formula I in an amount that is effective for treating said respiratory disease or condition. Within this embodiment is encompasses the above method wherein the respiratory disease or condition is selected from the group consisting of: asthma, chronic bronchitis, chronic obstructive pulmonary disease, adult respiratory distress syndrome, infant respiratory distress syndrome, cough, eosinophilic granuloma, respiratory syncytial virus bronchiolitis, bronchiectasis, idiopathic pulmonary fibrosis, acute lung injury and bronchiolitis obliterans organizing pneumonia.

The invention also encompasses a method for treating a disease or condition related to vascular integrity in a patient in need thereof, wherein the disease or condition is selected from the group consisting of: angioedemas, vasculitis, vascular damage caused by ischemic diseases and thrombosis, ischemic bowel diseases, inflammatory bowel diseases, necrotizing enterocolitis, intestinal lesions associated with thermal burns, arteriosclerosis, athersosclerosis, aortitis syndrome, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, sepsis, pancreatitis, disease caused by histamine or leukotriene-C4 release, necrosis caused by toxin, viral hepatitis, shock or anoxia, senile dementia, and trauma, comprising administering to the patient a compound of Formula I in an amount that is effective to treat the disease or condition.

The invention also encompasses a method for treating a disease or condition associated with cerebral or pulmonary edema in a patient in need thereof, comprising administering to the patient a compound of Formula I in an amount that is effective to treat the disease or condition. Within this embodiment is encompassed a disease or condition selected from the group consisting of: shock, sepsis, acute respiratory distress syndrome and brain edema.

Also, within this embodiment is encompassed the above method wherein the patient also has a respiratory disease or condition.

Also, within this embodiment is encompassed the above method wherein the patient is also suffering from a cardiovascular disease or condition.

The invention is described using the following definitions unless otherwise indicated.

When a nitrogen atom appears in a formula of the present specification, it is understood that sufficient hydrogen atoms or substituents are present to satisfy the valency of the nitrogen atom.

The term "halogen" or "halo" includes F, Cl, Br, and I.

The term "alkyl" means linear or branched structures and combinations thereof, having the indicated number of carbon atoms. Thus, for example, $C_{1-6}$alkyl includes methyl, ethyl, propyl, 2-propyl, s- and t-butyl, butyl, pentyl, hexyl, 1,1-dimethylethyl, cyclopropyl, cyclobutyl, cyclopentyl and cyclohexyl.

The term "alkenyl" means linear or branched structures and combinations thereof, of the indicated number of carbon atoms, having at least one carbon-to-carbon double bond, wherein hydrogen may be replaced by an additional carbon-to-carbon double bond. $C_{2-6}$alkenyl, for example, includes ethenyl, propenyl, 1-methylethenyl, butenyl and the like.

The term "alkynyl" means linear or branched structures and combinations thereof, of the indicated number of carbon atoms, having at least one carbon-to-carbon triple bond. $C_{3-6}$alkynyl, for example, includes, propenyl, 1-methylethenyl, butenyl and the like.

The term "alkoxy" means alkoxy groups of a straight, branched or cyclic configuration having the indicated number of carbon atoms. $C_{1-6}$alkoxy, for example, includes methoxy, ethoxy, propoxy, isopropoxy, and the like.

The term "alkylthio" means alkylthio groups having the indicated number of carbon atoms of a straight, branched or cyclic configuration. $C_{1-6}$alkylthio, for example, includes methylthio, propylthio, isopropylthio, and the like.

The term "cycloalkyl" means mono-, bi- or tri-cyclic structures, optionally combined with linear or branched structures, having the indicated number of carbon atoms. Examples of cycloalkyl groups include cyclopropyl, cyclopentyl, cycloheptyl, adamantyl, cyclododecylmethyl, 2-ethyl-1-bicyclo[4.4.0]decyl, cyclobutylmethyl cyclopropylmethyl and the like.

The term "cycloalkoxy" means cycloalkyl as defined above attached to a molecule by an oxygen atom (cycloalkyl-O) and includes, for example, cyclopentyloxy, cyclopropylmethyloxy and the like.

The term "acyl" means an organic radical derived from an organic acid by the removal of a hydroxyl group and having the general formula R—C(O)— wherein R is a linear or branched alkyl chain which together with the carbonyl carbon atom has the indicated number of carbon atoms. For example, $C_{2-4}$acyl, includes acetyl, propionyl and butyryl. The term "acyloxy" means acyl as defined above attached to a molecule by an oxygen atom (acyl-O) and includes, for example, acetyloxy and the like.

The phrase "$R^8$ and $R^9$ may be joined together with the nitrogen atom to which they are attached to form a saturated monocyclic ring of 3 to 8 atoms, optionally containing 1 or 2 oxygen atoms" means for example pyrrolidine, piperidine, morpholine, azetidine, etc.

The term "perfluoroalkyl" means alkyl as defined above, except that all hydrogen atoms have been replaced by fluoro atoms.

For purposes of this specification, the following abbreviations have the indicated meanings:

Me=methyl
Et=ethyl
n-Pr=normal propyl
i-Pr=isopropyl
n-Bu=normal butyl
i-Bu=isobutyl
s-Bu=secondary butyl
t-Bu=tertiary butyl
c-Pr=cyclopropyl
c-Bu=cyclobutyl
c-Pen=cyclopentyl
c-Hex=cyclohexyl The term "treating" encompasses not only treating a patient to relieve the patient of the signs and symptoms of the disease or condition but also prophylactically treating an asymptomatic patient to prevent the onset or progression of the disease or condition. The term "amount effective for treating" is intended to mean that amount of a drug or pharmaceutical agent that will elicit the biological or medical response of a tissue, a system, animal or human that is being sought by a researcher, veterinarian, medical doctor or other clinician. The term also encompasses the amount of a pharmaceutical drug that will prevent or reduce the risk of occurrence of the biological or medical event that is sought to be prevented in a tissue, a system, animal or human by a researcher, veterinarian, medical doctor or other clinician.

The invention described herein includes pharmaceutically acceptable salts and hydrates. Pharmaceutically acceptable salts include both the metallic (inorganic) salts and organic salts; a list of which is given in Remington's Pharmaceutical Sciences, 17th Edition, pg. 1418 (1985). It is well known to one skilled in the art that an appropriate salt form is chosen based on physical and chemical stability, flowability, hydroscopicity and solubility. As will be understood by those skilled in the art, pharmaceutically acceptable salts include, but are not limited to salts of inorganic acids such as hydrochloride, sulfate, phosphate, diphosphate, hydrobromide, and nitrate or salts of an organic acid such as malate, maleate, fumarate, tartrate, succinate, citrate, acetate, lactate, methanesulfonate, p-toluenesulfonate or pamoate, salicylate and stearate. Similarly pharmaceutically acceptable cations include, but are not limited to sodium, potassium, calcium, aluminum, lithium and ammonium (especially ammonium salts with secondary amines). Preferred salts of this invention for the reasons cited above include potassium, sodium, calcium and ammonium salts. Also included within the scope of this invention are crystal forms, hydrates and solvates of the compounds of Formula I.

For purposes of this Specification, "pharmaceutically acceptable hydrate" means the compounds of the instant invention crystallized with one or more molecules of water to form a hydrated form.

Compounds of Formula I may contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of Formula I.

Compounds of the Formula I may be separated into diastereoisomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent.

Alternatively, any enantiomer of a compound of the general Formula I may be obtained by stereospecific synthesis using optically pure starting materials or reagents of known configuration.

The invention also includes the compounds falling within Formula I in the form of one or more stereoisomers, in substantially pure form or in the form of a mixture of stereoisomers. All such isomers are encompassed within the present invention.

By virtue of their $S1P_1$/Edg1 agonist activity, the compounds of the present invention are immunoregulatory agents useful for treating or preventing autoimmune or chronic inflammatory diseases. The compounds of the present invention are useful to suppress the immune system in instances where immunosuppression is in order, such as in bone marrow, organ or transplant rejection, autoimmune and chronic inflammatory diseases, including systemic lupus erythematosis, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves opthalmopathy and asthma. The compounds of the invention are also useful for enhancing vascular integrity.

More particularly, the compounds of the present invention are useful to treat or prevent a disease or disorder selected from the group consisting of: transplantation of organs or tissue, graft-versus-host diseases brought about by transplantation, autoimmune syndromes including rheumatoid arthritis, systemic lupus erythematosus, Hashimoto's thyroiditis, multiple sclerosis, myasthenia gravis, type I diabetes, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia greata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyperresponsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-$C_4$ release, Beheet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, trauma, and chronic bacterial infection.

The compounds of the present invention are also useful for treating or preventing Alzheimer's Disease.

Also embodied within the present invention is a method of preventing or treating resistance to transplantation or transplantation rejection of organs or tissues in a mammalian patient in need thereof, which comprises administering a therapeutically effective amount of the compound of Formula I.

A method of suppressing the immune system in a mammalian patient in need thereof, which comprises administering to the patient an immune system suppressing amount of the compound of Formula I is yet another embodiment.

Most particularly, the method described herein encompasses a method of treating or preventing bone marrow or organ transplant rejection which is comprised of administering to a mammalian patient in need of such treatment or prevention a compound of Formula I, or a pharmaceutically acceptable salt or hydrate thereof, in an amount that is effective for treating or preventing bone marrow or organ transplant rejection.

The compounds of the present invention are also useful for treating a respiratory diseases or condition, such as asthma, chronic bronchitis, chronic obstructive pulmonary disease, adult respiratory distress syndrome, infant respiratory distress syndrome, cough, eosinophilic granuloma, respiratory syncytial virus bronchiolitis, bronchiectasis, idiopathic pulmonary fibrosis, acute lung injury and bronchiolitis obliterans organizing pneumonia.

Furthermore, the compounds of the present invention are selective agonists of the $S1P_1$/Edg1 receptor having selectivity over S1P3/Edg3 receptor. An Edg1 selective agonist has advantages over current therapies and extends the therapeutic window of lymphocytes sequestration agents, allowing better tolerability with higher dosing and thus improving efficacy as monotherapy.

The present invention also includes a pharmaceutical formulation comprising a pharmaceutically acceptable carrier and the compound of Formula I or a pharmaceutically acceptable salt or hydrate thereof, A preferred embodiment of the formulation is one where a second immunosuppressive agent is also included. Examples of such second immunosuppressive agents are, but are not limited to azathioprine, brequinar sodium, deoxyspergualin, mizaribine, mycophenolic acid morpholino ester, cyclosporin, FK-506, rapamycin, FTY720 and ISAtx247 (Isotechnika). Methods of co-administering a compound of Formula I with a second immunosuppressive agent, including one or more of the above, is also encompassed within the invention.

The present compounds, including salts and hydrates thereof, are useful in the treatment of autoimmune diseases, including the prevention of rejection of bone marrow transplant, foreign organ transplants and/or related afflictions, diseases and illnesses The compounds of this invention can be administered by any means that effects contact of the active ingredient compound with the site of action in the body of a warm-blooded animal. For example, administration can be oral, topical, including transdermal, ocular, buccal, intranasal, inhalation, intravaginal, rectal, intracisternal and parenteral. The term "parenteral" as used herein refers to modes of administration which include subcutaneous, intravenous, intramuscular, intraarticular injection or infusion, intrasternal and intraperitoneal.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will be dependent on the age, health and weight of the recipient, the extent of disease, kind of concurrent treatment, if any, frequency of treatment and the nature of the effect desired. Usually, a daily dosage of active ingredient compound will be from about 0.1-2000 milligrams per day. Ordinarily, from 1 to 100 milligrams per day in one or more applications is effective to obtain desired results. These dosages are the effective amounts for the treatment of autoimmune diseases, the prevention of rejection of foreign organ transplants and/or related afflictions, diseases and illnesses.

The active ingredient can be administered orally in solid dosage forms, such as capsules, tablets, troches, dragées, granules and powders, or in liquid dosage forms, such as elixirs, syrups, emulsions, dispersions, and suspensions. The active ingredient can also be administered parenterally, in sterile liquid dosage forms, such as dispersions, suspensions or solutions. Other dosages forms that can also be used to administer the active ingredient as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol, a standard reference text in this field.

For administration by inhalation, the compounds of the present invention may be conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

For ocular administration, an ophthalmic preparation may be formulated with an appropriate weight percent solution or suspension of the compounds of Formula I in an appropriate ophthalmic vehicle, such that the compound is maintained in contact with the ocular surface for a sufficient time period to allow the compound to penetrate the corneal and internal regions of the eye.

Useful pharmaceutical dosage-forms for administration of the compounds of this invention can be illustrated as follows:

Capsules

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol. The solution is made to volume with water for injection and sterilized.

Suspension

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise or in conjunction with another therapeutic agent. When drugs are administered in physical combination, the dosage form and administration route should be selected depending on the compatibility of the combined drugs. Thus the term coadministration is understood to include the administration of the two agents concomitantly or sequentially, or alternatively as a fixed dose combination of the two active components.

Methods of Synthesis

Several methods for preparing the compounds of this invention are described in the following Schemes and Examples. Starting materials and intermediates are made from known procedures or as otherwise illustrated.

Scheme 1 delineates a convenient method to prepare (5-(1,2,4-oxadiazol-3-yl)phenylpyrrolidin-3-yl)acetic acid compounds of the general structure 1-11 in this invention. An appropriately substituted anisole 1-1 is treated with pyroglutamic acid 1-2 at elevated temperature in the presence of triflic anhydride (*Bull. Korean Chem. Soc.* 1999, 20, 1253-1254) or phosphorus pentoxide and methanesulfonic acid (*Tetrahedron Lett.* 1989, 30, 7057-7060) to give lactam, 1-3. Conversion of the 5-methoxy group of 1-3 to the nitrile of 1-4 can be accomplished in a three-step sequence: 1) demethylation of 1-3 using a strong Lewis acid such as TMSI, $AlCl_3$, $BCl_3$, or $BBr_3$ in a suitable solvent such as dichloromethane or dichloroethane to afford a phenol; 2) formation of a trifluoromethanesulfonate ester (i.e. a triflate) using trifluoromethanesulfonic anhydride, 2-(N,N-bis(trifluoromethylsulfonyl)amino)-5-chloropyridine, or N-phenyl-bis(trifluoromethanesulfonimide) in the presence of a suitable base such as N,N-diisopropylethylamine, triethylamine, pyridine, or lutidine in a suitable solvent such as dichloromethane, dichloroethane, N-methylpyrrolidinone, or N,N-dimethylformamide; and 3) treatment of the triflate with zinc cyanide or copper cyanide and a palladium(0) catalyst employing a suitable ligand such as triphenylphosphine or 1,1'-bis(diphenylphosphino)ferrocene in a suitable solvent such as tetrahydrofuran, dioxane, N-methylpyrrolidinone, or N,N-dimethylformamide at or above room temperature. Introduction of an allyl group to provide 1-5 can be achieved in a two-step sequence: 1) protection of the lactam of 1-4 with a suitable protecting group (P) such as Boc, Cbz, Fmoc, or trifluoroacetyl; and 2) treatment of the resulting N-protected lactam with a strong base such as lithium N,N-diisopropylamide, potassium bis(trimethylsilyl)amide, sodium bis(trimethylsilyl)amide, or sodium hydride followed by addition of an allylic electrophile. A mixture of trans- and cis-adducts may be obtained and these two stereoisomers can be readily separated using methods known to those skilled in the art such as silica gel chromatography, HPLC, or crystallization. The trans-adduct may be predominantly formed when allyl iodide and lithium N,N-diisopropylamide are applied. The cis-adduct can be readily obtained by isolation from the reaction mixture or epimerization of the trans-adduct using an aforementioned strong base. Conversion of the olefin of 1-5 into an ester of 1-6 can be realized in a two-step sequence: 1) oxidative cleavage of the olefin of 1-5 to a carboxylic acid using methods known to those skilled in the art, which have been reviewed in the literature (see, March, J., "Oxidative Cleavage of Double Bonds and Aromatic Rings", pp. 1181-1183 in *Advanced Organic Chemistry*, John Wiley & Sons, 1992); and 2) esterification of the resulting carboxylic acid using (trimethylsilyl)diazomethane, diazomethane, or either MeOH or EtOH in the presence of a strong acid such as $H_2SO_4$ or HCl to supply 1-6. Removal of the protecting group P can be accomplished depending upon the chemical nature of P. For example, if P is a Boc group, hydrolysis of 1-6 using a strong protic acid such as trifluoroacetic acid or hydrochloric acid gives lactan 1-7. Nitrile 1-7 is treated with hydroxylamine hydrochloride in the presence of a suitable base such as triethylamine, N,N-diisopropylethylamine, sodium carbonate, potassium carbonate, or sodium bicarbonate in a suitable solvent such as MeOH or EtOH at or above room temperature to furnish amidoxime 1-8, which can be treated with an activated carboxylic acid in the presence of a suitable base and solvent to afford the N-acyloxyamidine of general structure 1-9. The carboxylic acid in this reaction can be activated for acylation with a reagent such as N,N-dicyclohexylcarbodiimide (EDC), 1-(3-dimethylaminopropyl)-3-ethylcarbodiimide, 1,1'-carbonyldiimidazole, or bis(2-oxo-3-oxazolidinyl)phosphinic chloride in the presence of a suitable base (if necessary) such as triethylamine, N,N-diisopropylethylamine, or sodium bicarbonate in a solvent such as 1,2-dichloroethane, toluene, xylenes, THF, acetonitrile, N,N-dimethylformamide, or N-methylpyrrolidinone. Alternatively, an acid chloride, acid anhydride, acyl imidazole, or pentafluorophenyl carboxylate ester could also be used in the presence of the aforementioned bases and solvents to provide 1-9. Intermediate 1-9 can be isolated using methods known to those skilled in the art such as silica gel chromatography, HPLC, or crystallization, and in a subsequent step cyclized/dehydrated by warming in a suitable solvent such as 1,2-dichloroethane, toluene, xylenes, THF, acetonitrile, N,N-dimethylformamide, or N-methylpyrrolidinone to deliver a 1,2,4-oxadiazole of the structure 1-10. Conversion of 1-9 to 1-10 may require addition of a suitable base such as pyridine, N,N-diisopropylethylamine, or tetrabutylammonium fluoride. It may be more convenient or desirable to not isolate N-acyloxyamidine 1-9 so that the transformation of 1-8 to 1-10 can be carried out as a continuous process. Other methods to prepare 1,2,4-oxadiazoles are potentially pertinent to the present invention and are known to those skilled in the art and have been reviewed in the literature (see, Clapp, L. B., "1,2,3- and 1,2,4-Oxadiazoles", pp. 366-91 in *Comprehensive Heterocyclic Chemistry, Volume 6*, Potts, K. T., Editor, Pergamon Press, 1984). The final compounds 1-11 can be obtained from 1-10 in a three-step sequence: 1) conversion of the lactam of 1-10 to an iminoether using trimethyloxonium tetrafluoroborate, methanesulfonyl fluoride, or dimethyl sulfate in a suitable solvent such as dichloromethane or dichloroethane; 2) reduction of the iminoether using a suitable reducing agent such as sodium cyanoborohydride or sodium borohydride in a suitable solvent such as methyl, ethyl, or isopropyl alcohol at the pH range between 4 and 5 (if necessary); and 3) hydrolysis of the carboxylic ester to the carboxylic acid (i.e., —CO$_2$A→—CO$_2$H) depending on the chemical structure of —CO$_2$A. Representative examples of this would include (but are not limited to): if -A is —CH$_3$ or —CH$_2$CH$_3$, treating with aqueous lithium, sodium, or potassium hydroxide in the presence of a suitable co-solvent such as methanol, ethanol, dioxane, or THF at or above room temperature to give 1-11.

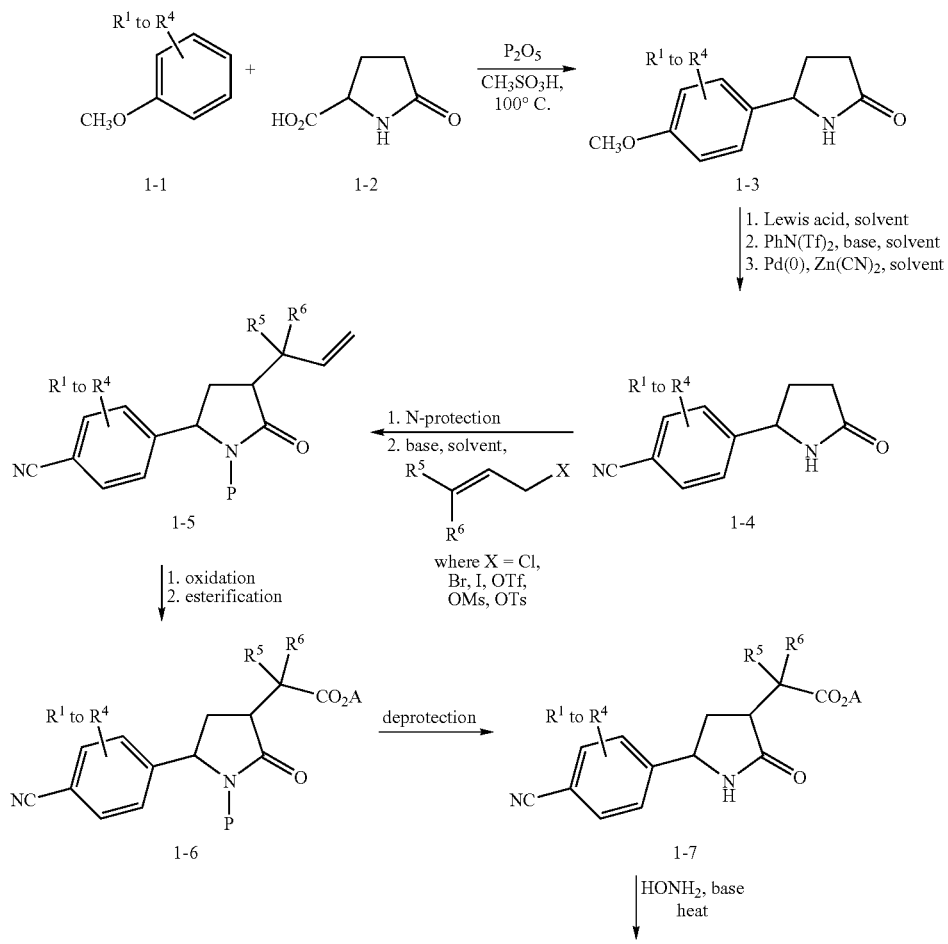

Scheme 1

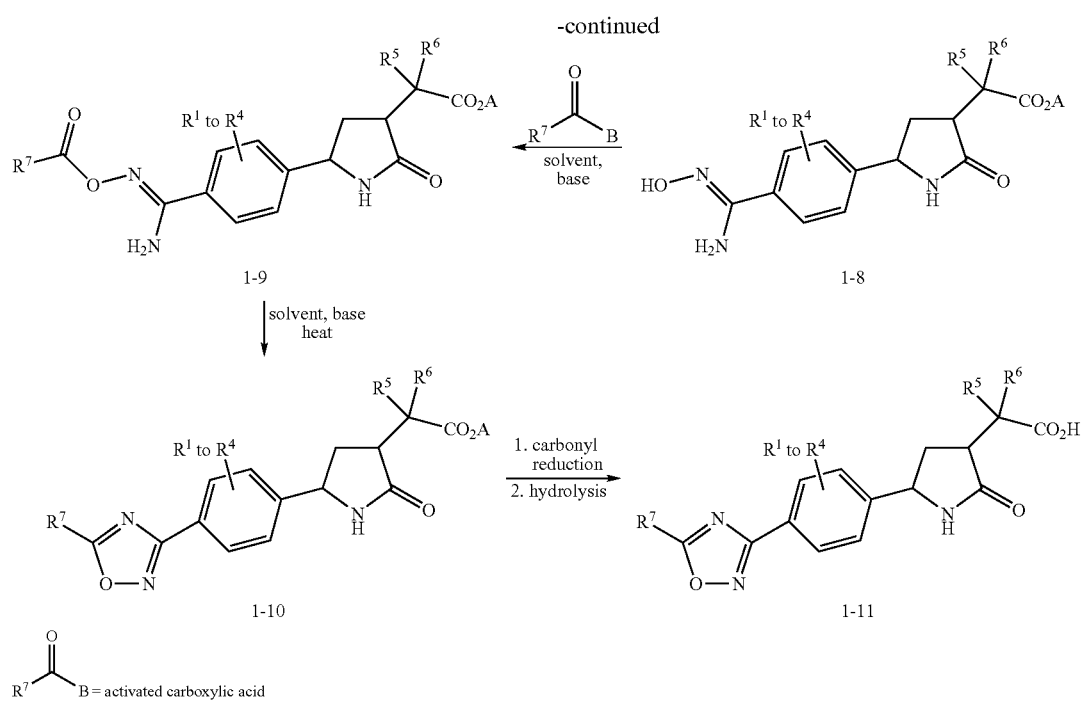

Scheme 2 describes three alternative methods to prepare amidoxime intermediates such as 2-2, 2-4, and 2-6. These intermediates can then be employed, in a manner similar to intermediate 1-8 in Scheme 1, to condense with carboxylic acids or activated carboxylic acids to form 1,2,4-oxadiazole intermediates such as 1-10 in Scheme 1, which can subsequently undergo appropriate functional group transformations analogous to those described in Scheme 1 to give the compounds of general structure 1-11 described in this invention. Removal of the protecting group P of 1-5 can be accomplished under either basic or acid conditions depending upon the chemical nature of P (Scheme 2-1). For example, if P is a Boc group, hydrolysis of 1-5 using a strong protic acid such as trifluoroacetic acid or hydrochloric acid affords lactam 2-1. Lactam 2-1 is then treated with hydroxylamine hydrochloride in the presence of a suitable base such as triethylamine, N,N-diisopropylethylamine, sodium carbonate, potassium carbonate, or sodium bicarbonate in a suitable solvent such as MeOH or EtOH at or above room temperature to furnish amidoxime 2-2. Amidoxime 2-2 (and also the other amidoximes listed in this scheme) can be subsequently converted into the compounds as described in this invention using a combination of appropriate procedures analogous to those depicted in Scheme 1 described to convert 1-8 to 1-11. On the other hand, lactam 2-1 can also be transformed into a protected pyrrolidine in a three-step sequence: 1) conversion of the lactam of 2-1 to an iminoether using trimethyloxonium tetrafluoroborate, methanesulfonyl fluoride, or dimethyl sulfate in a suitable solvent such as dichloromethane or dichloroethane; 2) reduction of the iminoether using a suitable reducing agent such as sodium cyanoborohydride or sodium borohydride in a suitable solvent such as methanol, ethanol, or isopropyl alcohol at the pH range between 4 and 5 (if necessary); and 3) protection of the resulting pyrrolidine with a suitable protecting group (P') such as Boc, Cbz, Fmoc, or trifluoroacetyl (Scheme 2-2). Pyrrolidine 2-3 is then treated with hydroxylamine hydrochloride in the presence of a suitable base such as triethylamine, N,N-diisopropylethylamine, sodium carbonate, potassium carbonate, or sodium bicarbonate in a suitable solvent such as MeOH or EtOH at or above room temperature to give amidoxime 2-4. Similarly, N-protected lactam 1-6 can be converted into N-protected pyrrolidine 2-5 in a four-step sequence (Scheme 2-3): 1) dependent upon the chemical nature of P, removal of the protecting group P of 1-6 can be accomplished under either basic or acid conditions as described previously (Scheme 2-1); 2) conversion of the resulting lactam to an iminoether using trimethyloxonium tetrafluoroborate, methanesulfonyl fluoride, or dimethyl sulfate in a suitable solvent such as dichloromethane or dichloroethane; 3) reduction of the iminoether using a suitable reducing agent such as sodium cyanoborohydride or sodium borohydride in a suitable solvent such as methanol, ethanol, or isopropyl alcohol at the pH range between 4 and 5 (if necessary); and 4) protection of the resulting pyrrolidine with a suitable protecting group (P') such as Boc, Cbz, Fmoc, or trifluoroacetyl. Finally, pyrrolidine 2-5 is then treated with hydroxylamine hydrochloride in the presence of a suitable base such as triethylamine, N,N-diisopropylethylamine, sodium carbonate, potassium carbonate, or sodium bicarbonate in a suitable solvent such as MeOH or EtOH at or above room temperature to give amidoxime 2-6.

Scheme 2

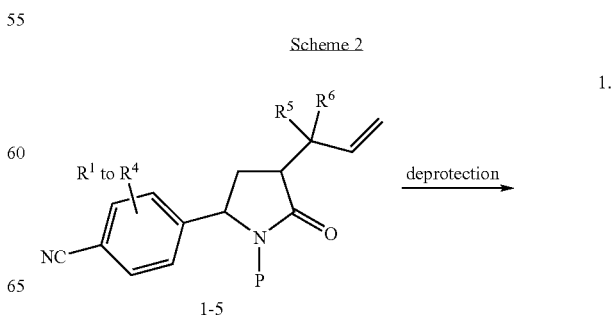

-continued

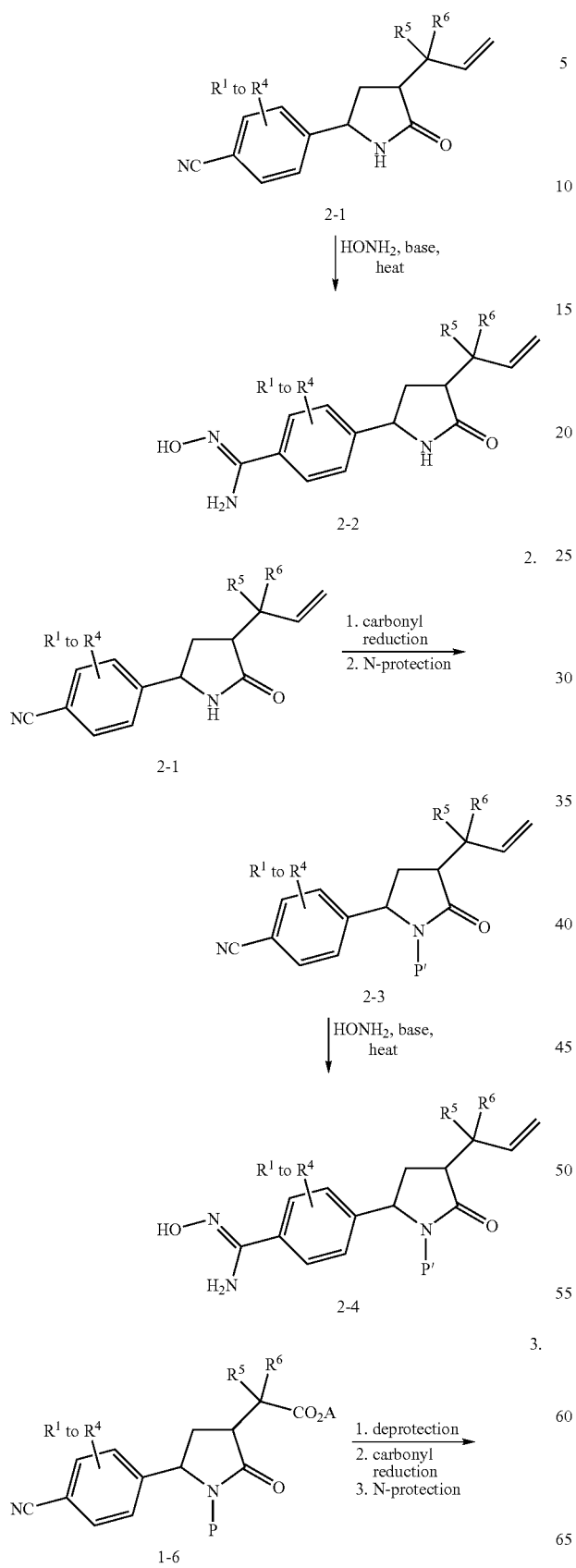

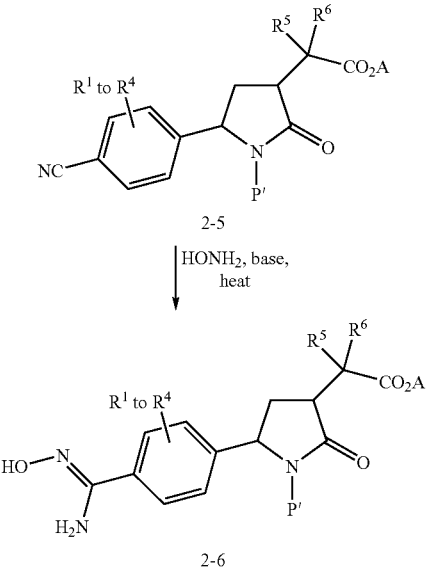

Scheme 3 outlines two alternative methods to synthesize 5-aryl-pyrrolidinones or 6-aryl-piperidone similar to 1-3 in Scheme 1. First, acylation of an appropriately substituted anisole 1-1 with succinic anhydride or glutaric anhydride 3-1 in the presence of a suitable Lewis acid such as aluminum trichloride, ferric chloride, zinc chloride, or boron trifluoride in a suitable solvent such as dichloromethane or dichloroethane gives a keto carboxylic acid, which is subsequently treated with methanol in the presence of a suitable acid such as tetrafluoroboric acid, hydrochloric acid, or concentrated $H_2SO_4$ at 0° C. or above to give methyl ester 3-2 (Scheme 3-1). Ketone 3-2 is treated with hydroxylamine hydrochloride in the presence of a suitable base such as triethylamine, N,N-diisopropylethylamine, sodium carbonate, sodium biocarbonate, potassium carbonate, or sodium acetate in a suitable solvent such as methanol, ethanol, or isopropyl alcohol at or above room temperature to give ketoxime 3-3. Hydrogenation of ketoxime 3-3 over a suitable catalyst such as palladium on carbon, palladium hydroxide on carbon, platinum(IV) oxide, or Raney nickel in the presence of a protic acid such as hydrochloric acid or acetic acid (if necessary) in a suitable solvent such as methanol, ethanol, or acetic acid gives an amine, which is subsequently treated with a suitable base such as triethylamine, N,N-diisopropylethylamine, pyridine, lutidine, potassium carbonate, or sodium carbonate in a suitable solvent such as THF, ether, pyridine, or toluene at or above room temperature to form a pyrrolidinone analogous to 1-3 or a piperidone. Alternatively, an appropriated substituted phenylmagnesium halide can react with 5-ethoxy-2-pyrrolidinone (*Org. Prep. Proc. Int.* 1993, 25, 255-258) or 6-ethoxy-2-piperidone (*J. Heterocyclic Chem.* 1970, 7, 615-622) to give a pyrrolidinone or analogous to 1-3 or a piperidone, respectively. The Grignard reagent 3-4 can be prepared using methods known to those skilled in the art and have been reviewed in the literature (see, March, J., "Aliphatic Electrophilic Substitution", pp. 622-625 in *Advanced Organic Chemistry*, John Wiley & Sons, 1992, and Knochel, P. and et al, "Functionalized Main-Group Organometallics for Organic Synthesis" *Pure Appl. Chem.* 2002, 74, 11-17). $R^1$ to $R^4$ and $R^{12}$ are functional group that are compatible with the reaction conditions and the latter can be readily converted into amidoxime for the subsequent synthesis of oxadiazoles using the methods known to those skilled in the art.

sodium cyanoborohydride or sodium borohydride in a suitable solvent such as methanol, ethanol, or isopropyl alcohol at the pH range between 4 and 5 (if necessary); and 3) protection of the resulting pyrrolidine with a suitable protecting group (P') such as Boc, Cbz, Fmoc, or trifluoroacetyl. Reduction of

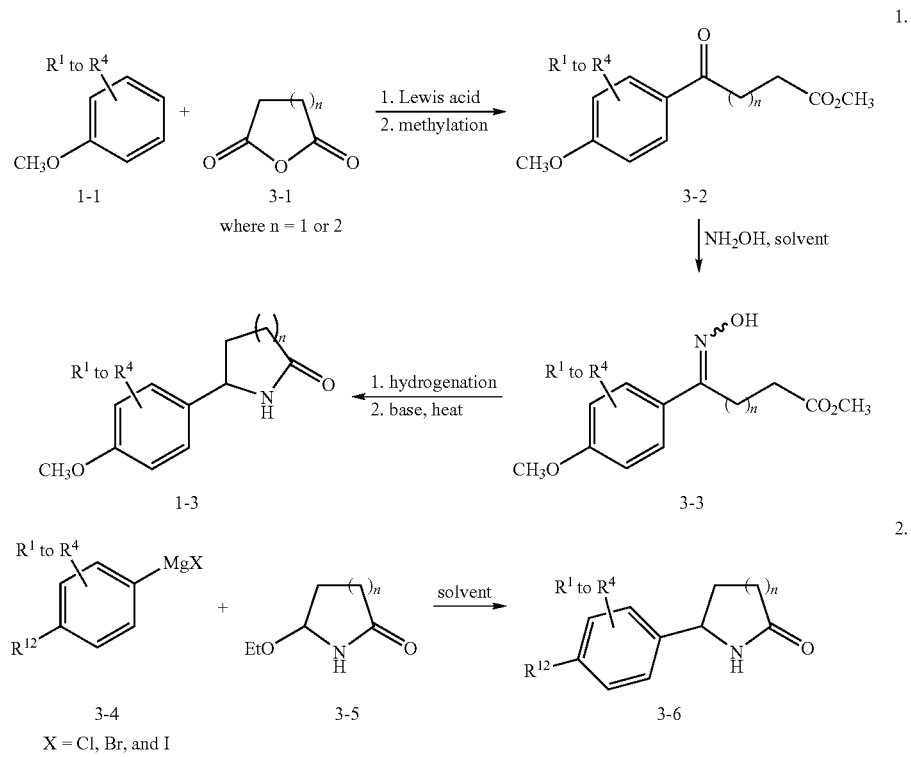

Scheme 4 illustrates three alternative methods to introduce an acetic acid functional group into pyrrolidinone or piperidone rings. First, an appropriately substituted 5-aryl-pyrrolidinone or 6-aryl-piperidone 4-1 can be treated with a strong base such as lithium N,N-diisopropylamide, potassium bis(trimethylsilyl)amide, sodium bis(trimethylsilyl)amide, or sodium hydride followed by addition of an alkyl 2-haloacetate or an alkyl 2-trifluorosulfonyloxyacetate, where alkyl group can be methyl, ethyl, or tert-butyl, and halide can be chloride, bromide, or iodide, in a suitable solvent such as dichloromethane, dichloroethane, THF, ether, or toluene at low temperature to afford 4-2 (Scheme 4-1). Conversion of lactam 4-2 to the compounds described in this invention can be accomplished using the methods known to those skilled in the art and analogous to those described in Scheme 1. Alternatively, pyrrolidinone or piperidone 4-1 can be treated with an aforementioned strong base followed by addition of alkyl chloroformate, where alkyl group can be methyl, ethyl, or isopropyl, in a suitable solvent such as dichloromethane, dichloroethane, THF, ether, or toluene at low temperature to afford 4-3. Transformation of pyrrolidinone or piperidone 4-3 to pyrrolidine or piperidine 4-4 can be achieved in a three-step sequence (Scheme 4-2): 1) conversion of the lactam of 4-3 to an iminoether using trimethyloxonium tetrafluoroborate, methanesulfonyl fluoride, or dimethyl sulfate in a suitable solvent such as dichloromethane or dichloroethane; 2) reduction of the iminoether using a suitable reducing agent such as the ester of 4-4 can be realized using a suitable reducing agent such as lithium aluminum hydride, diisobutylaluminum hydride, or lithium triethylborohydride in a suitable solvent such as dichloromethane, dichloroethane, toluene, THF, or ether at low temperature. Conversion of the hydroxyl group of 4-5 to cyanide 4-6 can be accomplished in a two-step sequence: 1) conversion of the hydroxyl group into a suitable leaving group such as mesylate, tosylate, triflate, bromide, or iodide using the methods known to those skilled in the art; and 2) displacement of the resulting leaving group using sodium cyanide, potassium cyanide, or tetrabutylammonium cyanide in a suitable solvent such as methyl sulfoxide, N,N-dimethylformamide, or acetone at or above room temperature. Hydrolysis of the cyanide group of 4-6 can be accomplished using aqueous lithium, sodium, or potassium hydroxide in a suitable co-solvent such as methanol, ethanol, or isopropyl alcohol at elevated temperature. Finally, pyrrolidinone or piperidone 4-1 can be treated with an aforementioned strong base followed by addition of an aldehyde or a ketone and subsequently a suitable protic acid such as hydrochloric acid in a suitable solvent such as dichloromethane, dichloroethane, THF, ether, or toluene to afford 4-8 (Scheme 4-3). The hydroxyl group can be readily converted into a carboxylic acid using the methods outlined in Scheme 1 and Scheme 4, which are known to those skilled in the art.

Scheme 4

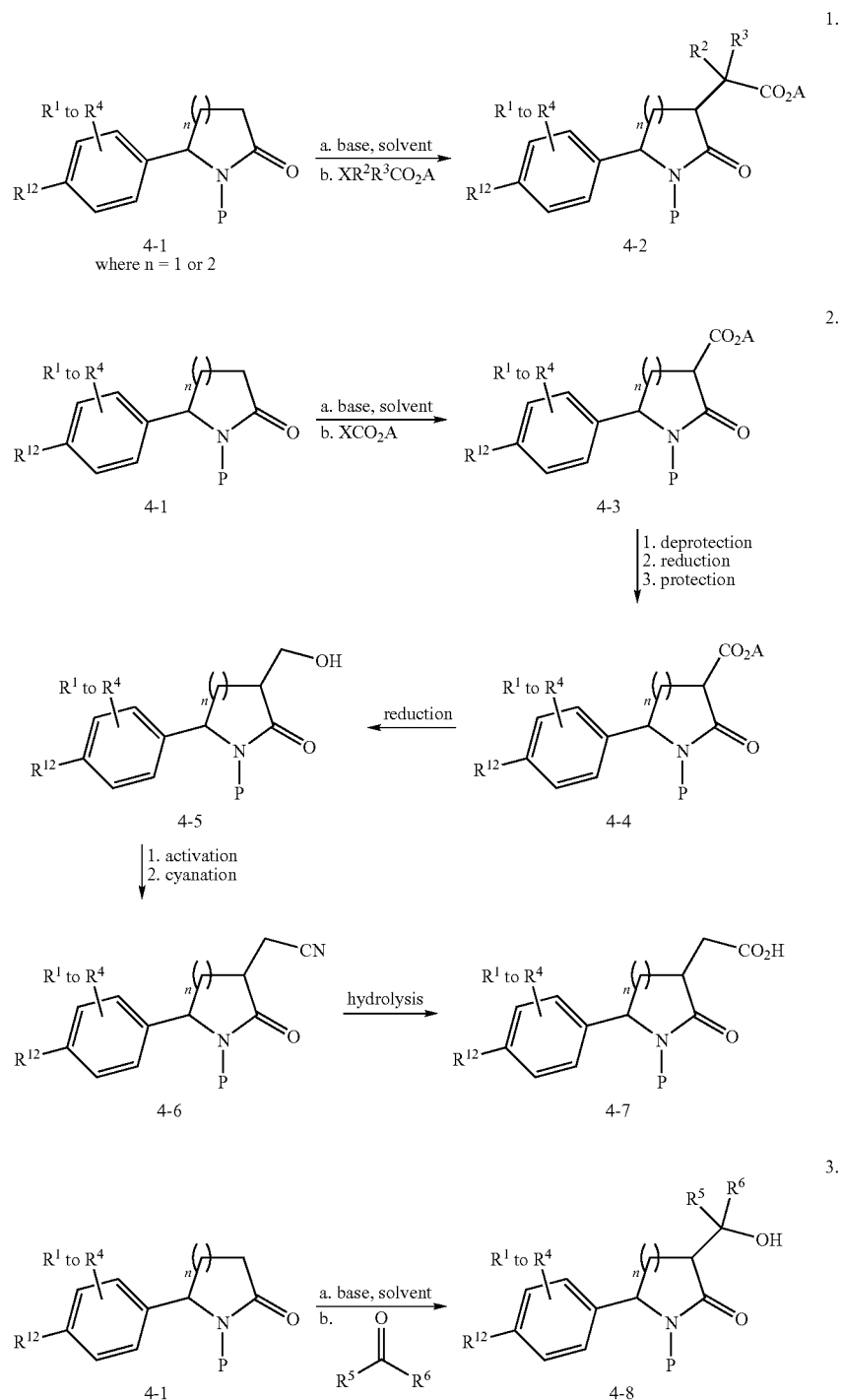

Finally, Scheme 5 depicts two hetero[2+3]cycloaddition methods to prepare 2-aryl-4-pyrrolidines having functional groups that can be readily transformed into an acetic acid. 6,6-Dimethyl-4,8-dioxa-1-methylenespiro[2,5]octane 5-1 can react with an appropriately substituted benzaldehyde O-methyloxime 5-2 in a suitable solvent such as acetonitrile, dichloromethane, dichloroethane, benzene, toluene, or xylenes at elevated temperature in a sealed reaction tube (if necessary) to give ketene acetal 5-3 (*J. Org. Chem.* 1998, 63, 1694-1703). Hydrolysis of ketene acetal 5-3 can be accomplished in the presence of a suitable aqueous protic acid such as acetic acid or hydrochloric acid in a suitable solvent such as THF or acetonitrile. Pyrrolidine 5-4 can be converted into the compounds described in this invention using the methods known to those skilled in the art. On the other hand, N-tosylimine 5-5 can react with ((trimethylsilyl)methyl)allyl acetate 5-6 in the presence of a palladium(0) catalyst employing a suitable ligand such as triphenylphosphine or triisopropyl phosphite in a suitable solvent such as THF or dioxane at elevated temperature (*J. Am. Chem. Soc.* 1993, 115, 6636-6645). Pyrrolidine 5-7 can be converted into the compounds described in this invention using the methods known to those skilled in the art.

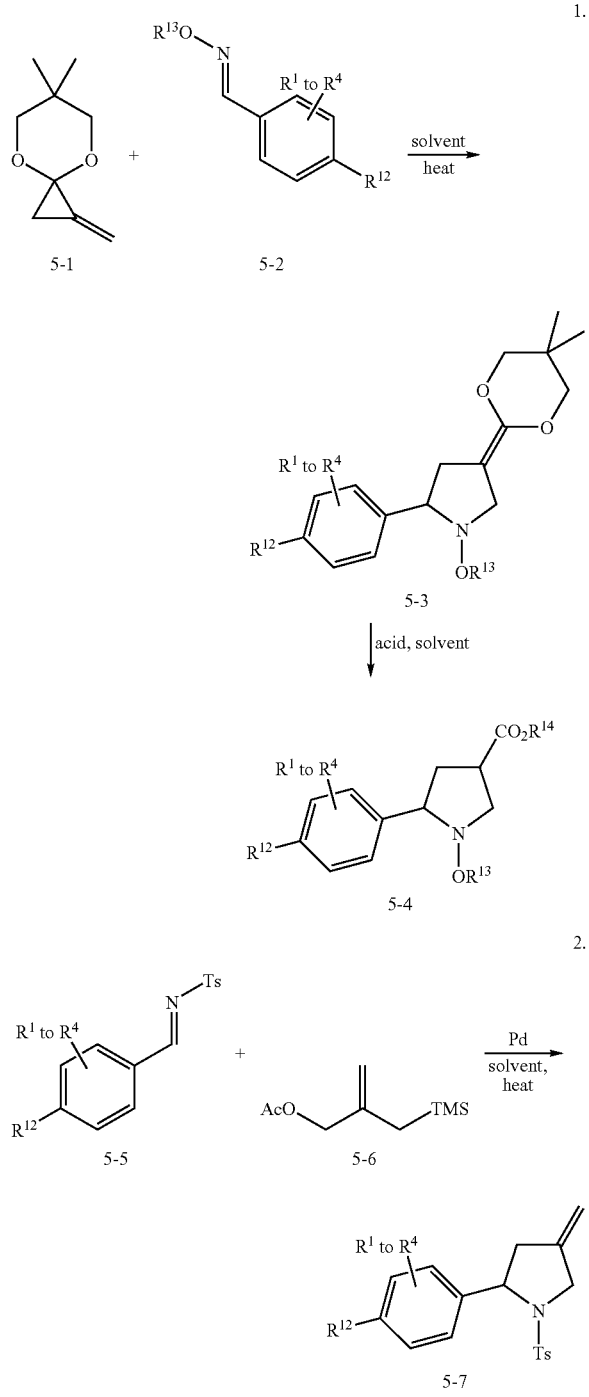

REPRESENTATIVE EXAMPLES

Compounds of the invention are exemplified as follows:

General Methods

Reactions sensitive to moisture or air were performed under nitrogen or argon using anhydrous solvents and reagents. The progress of reactions was determined by either LC-MS or analytical thin layer chromatography (TLC) performed with E. Merck precoated TLC plates, silica gel 60F-254, layer thickness 0.25 mm. Concentration of solutions was carried out on a rotary evaporator under reduced pressure. Flash chromatography was carried out using a Biotage Flash Chromatography apparatus (Dyax Corp.) on silica gel (32-63 mM, 60 Å pore size) in pre-packed cartridges of the size noted. $^1$H NMR spectra were acquired at 500 MHz spectrometers in $CDCl_3$ solutions unless otherwise noted. Chemical shifts were reported in parts per million. Tetramethylsilane (TMS) was used as internal reference in $CD_3Cl$ solutions, and residual $CH_3OH$ peak or TMS was used as internal reference in $CD_3OD$ solutions. Coupling constants (J) were reported in hertz (Hz). Abbreviations: ethyl acetate (EtOAc), diethyl ether (ether or $Et_2O$), triethylamine (TEA), N,N-diisopropylethylamine (DIEA), N,N-dimethylformamide (DMF), tetrahydrofuran (THF), trifluoroacetic acid (TFA), saturated aqueous (sat'd), room temperature (rt), hour(s) (h or hr), and minute(s) (min). High performance liquid chromatography (HPLC) was performed on ADV731020 100×20 mm column with gradient 10:90-95:5 v/v $CH_3CN/H_2O$+v0.05% TFA over 23 min then hold at 95:5 v/v $CH_3CN/H_2O$+0.05% TFA for 7 min; 10 mL/min, 254 nm.

Preparation of Amidoxime Intermediates

Amidoxime 1

Methyl trans-5-(4-(amino(hydroxyimino)methyl)phenyl)-2-oxo-3-pyrrolidineacetate

Step A: 5-(4-Trifluoromethanesulfonyloxyphenyl)-2-pyrrolidinone

DIEA (2.89 mL, 16.6 mmol) was added to a solution of 5-(4-hydroxyphenyl)-2-pyrrolidinone (1.47 g, 8.30 mmol) and N-phenyltrifluoromethanesulfonimide (4.45 g, 12.45 mmol) in 10 mL of DMF, and the mixture was stirred at rt overnight. The reaction mixture was diluted with EtOAc (100 mL) and washed with brine (50 mL), $H_2O$ (3×50 mL), and brine (50 mL). The organic layer was separated, dried over $MgSO_4$, and concentrated. Chromatography on a Biotage 40+M cartridge using EtOAc as the eluant afforded 2.45 g (96%) of the title compound as a white solid: $^1$H NMR δ 1.90-1.98 (m, 1H), 2.38-2.51 (m, 2H), 2.57-2.65 (m, 1H), 4.81 (t, 1=7.1, 1H), 6.92 (br. s, 1H), 7.27-7.30 (m, 2H), 7.38-7.42 (m, 2H).

Step B: 5-(4-Cyanophenyl)-2-pyrrolidinone

A solution of 5-(4-trifluoromethanesulfonyloxyphenyl)-2-pyrrolidinone (2.45 g, 8.22 mmol), tetrakis(triphenylphosphine)palladium (475 mg, 0.41 mmol), and zinc cyanide (1.45 g, 12.3 mmol) in 10 mL of DMF was flushed with nitrogen three times and then stirred at 80° C. After 3 hr, the mixture was cooled down to rt, diluted with EtOAc (10 mL), and filtered through a cake of Celite. The solid was washed with EtOAc, and the filtrates were combined and concentrated. Chromatography on a Biotage 40+M cartridge using 9:1 v/v EtOAc/CH$_3$OH as the eluant gave 2.68 g (100%) of the title compound containing trace amount of DMF: $^1$H NMR (CD$_3$OD) δ 1.90-1.97 (m, 1H), 2.43-2.51 (m, 2H), 2.60-2.67 (m, 1H), 4.85 (t, J=7.2, 1H), 7.41 (d, J=8.8, 2H), 7.65 (d, J=8.5, 2H).

Step C: N-tert-Butyloxycarbonyl-5-(4-cyanophenyl)-2-pyrrolidinone 4-(Dimethylamino)pyridine (50 mg, 0.41 mmol) was added to a solution of the aforementioned nitrile (2.68 g, 8.22 mmol) and di-tert-butyl dicarbonate (3.59 g, 16.4 mmol) in 20 mL of CH$_2$Cl$_2$. The mixture was stirred at rt overnight and then concentrated. Chromatography on a Biotage 40+M cartridge using 9:11 v/v EtOAc/hexanes as the eluant afforded 1-16 g (74%) of the title compound: 114 NMR δ 1.30 (s, 9H), 1.82-1.89 (m, 1H), 2.48-2.69 (m, 31H), 5.19 (dd, J=4.2, 8.3, 11H), 7.35 (d, J=8.2, 2H), 7.68 (d, J=8.3, 2H).

Step D: Trans-N-tert-butyloxycarbonyl-5-(4-cyanophenyl)-3-(2-propenyl)-2-pyrrolidinone A solution of freshly prepared lithium diisopropylamide (2.80 mmol) in 10 mL of THF was added dropwise into a solution of N-tert-butyloxycarbonyl-5-(4-cyanophenyl)-2-pyrrolidinone (763 mg, 2.67 mmol) in 10 mL of THF at −78° C. After stirring for 1 hr at −78° C., allyl iodide (488 µL, 5.33 mmol) was added. The mixture was stirred at −78° C. for 1 hr, and then quenched with 5.0 mL of sat'd NH$_4$Cl solution. The mixture was poured into a mixture of brine (20 mL) and CH$_2$Cl$_2$ (20 mL), and the aqueous layer was separated and extracted with CH$_2$Cl$_2$ (3×20 mL). Organic layers were combined, dried over MgSO$_4$, and concentrated. Chromatography on a Biotage 40+M cartridge using 1:4 v/v EtOAc/hexanes as the eluant gave 745 mg (86%) of the title compound: $^1$H NMR δ 1.35 (s, 9H), 1.99-2.05 (m, 1H), 2.21-2.29 (m, 1H), 2.63-2.76 (m, 2H), 5.06-5.11 (m, 2H), 5.17-5.20 (m, 1H), 5.68-5.77 (m, 1H), 7.32 (d, J=8.2, 2H), 7.67 (d, J=8.4, 2H).

Step E: Trans-N-tert-butyloxycarbonyl-5-(4-cyanophenyl)-2-oxo-3-pyrrolidineacetic acid Ruthenium(III) chloride hydrate (3.5 mg, 0.02 mmol) was added into a solution of trans N-tert-butyloxycarbonyl-5-(4-cyanophenyl)-3-(2-propenyl)-2-pyrrolidinone (252 mg, 0.77 mmol) and sodium periodate (744 mg, 3.48 mmol) in a mixed solvent (14.0 mL) of 2:2:3 v/v/v CCl$_4$/CH$_3$CN/H$_2$O. The mixture was stirred at rt for 1 hr and then partitioned between H$_2$O (20 mL) and CH$_2$Cl$_2$ (20 mL). The aqueous layer was separated and extracted with CH$_2$Cl$_2$ (3×20 mL). Organic layers were combined, dried over Na$_2$SO$_4$, and concentrated to give the crude acid as a colorless syrup, which was used in the next step without further purification.

Step F: Methyl trans-N-tert-butyloxycarbonyl-5-(4-cyanophenyl)-2-oxo-3-pyrrolidineacetate (Trimethylsilyl)diazomethane (2.0 M in hexanes, 580 µL, 1.16 mmol) was added to a solution of the aforementioned crude acid in a mixed solvent (18 mL) of 7:2 v/v benzene/CH$_3$OH. After 30 min, the reaction mixture was concentrated. Chromatography on a Biotage 40+M cartridge using 9:11 v/v EtOAc/hexanes as the eluant gave 261 mg (94% over two steps) of the title compound as a white solid: 11H NMR δ 1.36 (s, 9H), 2.21 (ddd, J=1.1, 8.7, 13.0, 1H), 2.29-2.36 (m, 1H), 2.52 (dd, J=8.7, 17.2, 1H), 2.92 (dd, J=4.2, 17.1, 1H), 3.02-3.06 (m, 1H), 3.68 (s, 3H), 5.24 (d, J=8.4, 1H), 7.32 (d, J=8.2, 2H), 7.68 (d, J=8.5, 2H).

Step G: Methyl trans-5-(4-cyanophenyl)-2-oxo-3-pyrrolidineacetate

A solution of the aforementioned methyl ester (261 mg, 0.73 mmol) in 10 mL of 20% TFA in CH$_2$Cl$_2$ was stirred at rt for 1 hr. The mixture was concentrated, and the residue was dissolved in CH$_2$Cl$_2$ (50 mL) and washed with sat'd NaHCO$_3$ (10 mL×2) and brine (10 mL). The organic layer was dried over Na$_2$SO$_4$ and concentrated. Chromatography on a Biotage 40+S cartridge using 4:1 v/v EtOAc/hexanes as the eluant afforded 167 mg (89%) of the title compound as a white solid: $^1$H NMR δ 2.25-2.31 (m, 1H), 2.42-2.54 (m, 2H), 2.82-2.92 (m, 2H), 3.68 (s, 3H), 4.84 (dd, J=2.4, 8.8, 1H), 7.07 (s, 1H), 7.40 (d, J=8.2, 2H), 7.67 (d, J=8.2, 2H).

Step H: Methyl trans-5-(4-(amino(hydroxyimino)methyl)phenyl)-2-oxo-3-pyrrolidineacetate Hydroxylamine hydrochloride (45 mg, 0.65 mmol) was added to a solution of the resulting lactam (167 mg, 0.65 mmol) and sodium hydrogencarbonate (272 mg, 3.24 mmol) in 10 mL of CH$_3$OH. The mixture was refluxed for 5 hr and then cooled down to rt. The precipitate was filtered off through a 0.2µ filter and washed thoroughly with CH$_3$OH (100 mL). The filtrate was concentrated to give the desired amidoxime as a white solid, which was used without further purification.

Amidoxime 2

Methyl cis-5-(4-(amino(hydroxyimino)methyl)phenyl)-2-oxo-3-pyrrolidineacetate

Step A: Cis-N-tert-butyloxycarbonyl-5-(4-cyanophenyl)-3-(2-propenyl)-2-pyrrolidinone A solution of freshly prepared lithium diisopropylamide (0.75 mmol) in 5 mL of THF was added dropwise into a solution of trans N-tert-butyloxycarbonyl-5-(4-cyanophenyl)-3-(2-propenyl)-2-pyrrolidinone (223 mg, 0.68 mmol) in 5 mL of THF at −78° C. After stirring at −78° C. for 1 hr, the reaction was quenched by adding 5.0 mL of sat'd NH$_4$Cl solution. The mixture was allowed to warm up to rt, and poured into a mixture of brine (20 mL) and CH$_2$Cl$_2$ (20 mL). The aqueous layer was separated and extracted with CH$_2$Cl$_2$ (3×20 mL). Organic layers were combined, dried over Na$_2$SO$_4$ and concentrated. Chromatography on a Biotage 40+S cartridge using 1:3 v/v EtOAc/hexanes as the eluant gave 103 mg (46%) of the title compound and 120 mg (54%) of starting material: $^1$H NMR δ 1.24 (s, 9H), 1.50-1.57 (m, 1H), 2.22-2.28 (m, 1H), 2.56-2.77 (m, 3H), 4.94-5.07 (m, 3H), 5.71-5.78 (m, 1H), 7.36 (d, J=8.2, 2H), 7.66 (d, J=8.2, 2H).

Step B: Cis-N-tert-butoxycarbonyl-5-(4-cyanophenyl)-2-oxo-3-pyrrolidineacetic acid The title compound was prepared using a procedure analogous to that described in AMIDOXIME 1, Step E substituting cis-N-tert-butyloxycarbonyl-5-(4-cyanophenyl)-3-(2-propenyl)-2-pyrrolidinone for trans-N-tert-butyloxycarbonyl-5-(4-cyanophenyl)-3-(2-propenyl)-2-pyrrolidinone. The crude acid was taken onto next step without further purification.

Step C: Methyl cis-N-tert-butyloxycarbonyl-5-(4-cyanophenyl)-2-oxo-3-pyrrolidineacetate The title compound was prepared using a procedure analogous to that described in AMIDOXIME 1, Step F substituting cis-N-tert-butyloxycarbonyl-5-(4-cyanophenyl)-2-oxo-3-pyrrolidineacetic acid for trans-N-tert-butyloxycarbonyl-5-(4-cyanophenyl)-2-oxo-3-pyrrolidincacetic acid: $^1$NMR δ 1.24 (s, 9H), 1.62-1.69 (m, 1H), 2.62 (dd, J=8.1, 17.2, 1H), 2.69-2.76 (m, 1H), 2.92 (dd, J=3.9, 17.4, 1H), 2.98-3.04 (m, 1H), 3.69 (s, 3H), 4.98 (dd, J=7.5, 9.5, 1H), 7.43 (d, J=8.3, 2H), 7.67 (d, J=8.4, 2H).

Step D: Methyl cis-5-(4-cyanophenyl)-2-oxo-3-pyrrolidineacetate

The title compound was prepared using a procedure analogous to that described in AMIDOXIME 1, Step G substituting methyl cis-N-tert-butyloxycarbonyl-5-(4-cyanophenyl)-2-oxo-3-pyrrolidineacetate for methyl trans-N-tert-butyloxycarbonyl-5-(4-cyanophenyl)-2-oxo-3-pyrrolidineacetate: $^1$H NMR δ 1.67-1.74 (m, 11H), 2.52 (dd, J=8.6, 17.1, 11H), 2.80-2.98 (m, 3H), 3.68 (s, 3H), 4.75 (dd, J=6.8, 9.3, 1H), 6.51 (s, 1H), 7.48 (d, J=8.2, 2H), 7.67 (d, J=8.2, 2H).

Step E: Methyl cis-5-(4-(amino(hydroxyimino)methyl)phenyl)-2-oxo-3-pyrrolidineacetate The title compound was prepared using a procedure analogous to that described in AMIDOXIME 1, Step H substituting methyl trans-5-(4-cyanophenyl)-2-oxo-3-pyrrolidineacetate for methyl cis-5-(4-cyanophenyl)-2-oxo-3-pyrrolidineacetate. The crude amidoxime was used without further purification.

Amidoxime 3

Trans-5-(4-(amino(hydroxyimino)methyl)phenyl)-2-oxo-3-(2-propenyl)-pyrrolidine

Step A: Trans-5-(4-cyanophenyl)-2-oxo-3-(2-propenyl)-pyrrolidine

The title compound was prepared using a procedure analogous to that described in AMIDOXIME 1, Step G substituting trans-N-tert-butyloxycarbonyl-5-(4-cyanophenyl)-2-oxo-3-(2-propenyl)-pyrrolidine for methyl trans-N-tert-butyloxycarbonyl-5-(4-cyanophenyl)-2-oxo-3-pyrrolidineacetate: $^1$H NMR δ 2.05-2.12 (m, 114), 2.23-2.29 (m, 1H), 2.38-2.44 (m, 1H), 2.54-2.64 (m, 2H), 4.77 (dd, J=4.3, 8.6, 1H), 5.08-5.14 (m, 2H), 5.74-5.80 (m, 1H), 6.55 (br. s, 1H), 7.40 (d, J=8.2, 2H), 7.66 (d, J=8.3, 2H).

Step B: Trans-5-(4-(amino(hydroxyimino)methyl)phenyl)-2-oxo-3-(2-propenyl-pyrrolidine The title compound was prepared using a procedure analogous to that described in AMIDOXIME 1, Step H substituting trans-5-(4-cyanophenyl)-2-oxo-3-(2-propenyl)-pyrrolidine for methyl trans-5-(4-cyanophenyl)-2-oxo-3-pyrrolidineacetate. The crude amidoxime was used without further purification.

Amidoxime 4

Methyl trans-N-tert-butyloxycarbonyl-2-(4-(amino(hydroxyimino)methyl)phenyl)-4-pyrrolidineacetate

Step A: Methyl trans-2-(4-cyanophenyl)-2-H-3,4-dihydro-5-methoxy-4-pyrrolidineacetate A solution of methyl trans-5-(4-cyanophenyl)-2-oxo-3-pyrrolidineacetate (see AMIDOXIME 1, step E) (196 mg, 0.76 mmol) and trimethyloxonium tetrafluoroborate (135 mg, 0.91 mmol) in 10 mL of $CH_2Cl_2$ was stirred at rt overnight. The mixture was washed with 20 mL of sat'd $NaHCO_3$, and the aqueous layer was extracted with $CH_2Cl_2$ (3×20 mL). The organic layers were combined, dried over $Na_2SO_4$, and concentrated to give the desired methoxy imine (207 mg, 100%) as a colorless syrup: $^1$H NMR δ 2.15-2.21 (m, 1H), 2.33-2.39 (m, 1H), 2.46 (dd, J=9.5, 16.2, 1H), 2.75 (dd, J=4.7, 16.2, 1H), 3.22-3.28 (m, 1H), 3.70 (s, 3H), 3.93 (s, 3H), 5.06 (dd, J=5.3, 8.3, 1H), 7.36 (d, J=8.2, 2H), 7.61 (d, J=8.3, 2H).

Step B: Methyl trans-2-(4-cyanophenyl)-4-pyrrolidineacetate

A solution of sodium cyanoborohydride (1.0 M in THF, 7.6 mL, 7.6 mmol) was added to a solution of the methoxy imine (207 mg, 0.76 mmol) and a bit of bromocresol green in $CH_3OH$ (10 mL). A solution of HCl in 1,4-dioxane (2.0 M) was added to the reaction mixture to maintain the color was yellow, and the resulting mixture was stirred at rt for 4 hr. Poured into sat'd $NaHCO_3$ and $CH_2Cl_2$ and the aqueous layer was further extracted with $CH_2Cl_2$ (3×20 mL). Organic layers were combined, dried over $Na_2SO_4$, and concentrated to give the crude amine (158 mg, 85%), which was taken onto next step without further purification.

Step C: Methyl trans-N-tert-butyloxycarbonyl-2-(4-cyanophenyl)-4-pyrrolidineacetate Di-tert-butyl dicarbonate (170 mg, 0.78 mmol) was added to a solution of the resulting amine (158 mg, 0.65 mmol) and catalytic amount of 4-dimethylaminopyridine in $CH_2Cl_2$ (10 mL). The mixture was stirred at rt for 3 hr. The mixture was concentrated. Chromatography on a Biotage 40+S cartridge using 3:7 v/v EtOAc/hexanes as the eluant afforded 208 mg (93%) of the title compound: $^1$H NMR δ 1.20-1.45 (m, 9H), 1.99-2.14 (m, 2H), 2.37-2.63 (m, 3H), 3.17-3.27 (m, 1H), 3.67 (s, 3H), 3.86-3.88 (m, 1H), 4.87-4.89 (m, 1H), 7.28 (d, J=8.2, 2H), 7.61 (d, J=8.0, 2H).

Step D: Methyl trans-N-tert-butyloxycarbonyl-2-(4-(amino(hydroxyimino)methyl)phenyl)-4-pyrrolidineacetate The title compound was prepared using a procedure analogous to that described in AMIDOXIME 1, Step H substituting methyl trans-N-tert-butyloxycarbonyl-2-(4-cyanophenyl)-4-pyrrolidineacetate for methyl trans-5-(4-cyanophenyl)-2-oxo-3-pyrrolidineacetate. The crude amidoxime was used without further purification.

Amidoxime 5

Methyl cis-N-tert-butyloxycarbonyl-2-(4-(amino (hydroxyimino)methyl)phenyl)-4-pyrrolidineacetate

Step A: Methyl cis-2-(4-cyanophenyl)-2-H-3,4-dihydro-5-methoxy-4-pyrrolidineacetate The title compound was prepared using a procedure analogous to that described in AMIDOXIME 4, Step A substituting methyl cis-5-(4-cyanophenyl)-2-oxo-3-pyrrolidineacetate (see AMIDOXIME 2, step C) for methyl trans-5-(4-cyanophenyl)-2-oxo-3-pyrrolidineacetate: $^1$H NMR δ 1.51-1.58 (m, 1H) 2.41 (dd, J=8.8, 16.6, 1H), 2.79 (dd, J=4.5, 16.6, 1H), 2.83-2.90 (m, 1H), 3.27-3.34 (m, 1H), 3.68 (s, 3H), 3.93 (s, 3H), 4.88 (t, J=8.2, 1H), 7.44 (d, J=8.2, 2H), 7.62 (d, J=8.3, 2H).

Step B: Methyl cis-2-(4-cyanophenyl)-4-pyrrolidineacetate

The title compound was prepared using a procedure analogous to that described in AMIDOXIME 4, Step B substituting methyl cis-2-(4-cyanophenyl)-2-H-3,4-dihydro-5-methoxy-4-pyrrolidineacetate for methyl trans-2-(4-cyanophenyl)-2-H-3,4-dihydro-5-methoxy-4-pyrrolidineacetate.

Step C: Methyl cis-N-tert-butyloxycarbonyl-2-(4-cyanophenyl)-4-pyrrolidineacetate The title compound was prepared using a procedure analogous to that described in AMIDOXIME 4, Step C substituting methyl cis-2-(4-cyanophenyl)-4-pyrrolidineacetate for methyl trans-2-(4-cyanophenyl)-4-pyrrolidineacetate: $^1$H NMR δ 1.12-1.51 (m, 10H), 2.35-2.64 (m, 4H), 3.15 (t, J=9.9, 1H), 3.68 (s, 3H), 4.02-4.08 (m, 1H), 4.72-4.81 (m, 1H), 7.30 (d, J=8.1, 2H), 7.60 (d, J=8.2, 2H).

Step D: Methyl trans-N-tert-butoxycarbonyl-2-(4-(amino(hydroxyimino)methyl)phenyl)-4-pyrrolidineacetate The title compound was prepared using a procedure analogous to that described in AMIDOXIME 1, Step H substituting methyl cis-N-tert-butoxycarbonyl-2-(4-cyanophenyl)-4-pyrrolidineacetate for methyl trans-5-(4-cyanophenyl)-2-oxo-3-pyrrolidineacetate. The crude amidoxime was used without further purification.

Amidoxime 6

Trans-N-tert-Butyloxycarbonyl-2-(4-(amino(hydroxyimino)methyl)phenyl)-4-(2-propenyl)-pyrrolidine

Step A: Trans-2-(4-cyanophenyl)-2-H-3,4-dihydro-5-methoxy-4-(2-propenyl)-pyrrolidine The title compound was prepared using a procedure analogous to that described in AMIDOXIME 4, Step A substituting trans-N-tert-butyloxycarbonyl-5-(4-cyanophenyl)-3-(2-propenyl)-2-pyrrolidinone (see AMIDOXIME 1, step C) for methyl trans-5-(4-cyanophenyl)-2-oxo-3-pyrrolidineacetate. The crude product was used in next step without further purification.

Step B: Trans-2-(4-cyanophenyl)-4-(2-propenyl)-pyrrolidine

The title compound was prepared using a procedure analogous to that described in AMIDOXIME 4, Step B substituting trans-2-(4-cyanophenyl)-2-H-3,4-dihydro-5-methoxy-4-(2-propenyl)-pyrrolidine for methyl trans-2-(4-cyanophenyl)-2-H-3,4-dihydro-5-methoxy-4-pyrrolidineacetate.

Step C: Trans-N-tert-butoxycarbonyl-2-(4-cyanophenyl)-4-(2-propenyl)-pyrrolidine The title compound was prepared using a procedure analogous to that described in AMIDOXIME 4, Step C substituting trans-2-(4-cyanophenyl)-4-(2-propenyl)-pyrrolidine for methyl trans-2-(4-cyanophenyl)-4-pyrrolidineacetate: $^1$H NMR δ 1.20-1.46 (m, 9H), 1.89-2.28 (m, 5H), 3.14-3.27 (m, 1H), 3.71-3.81 (m, 1H), 5.00-5.07 (m, 3H), 5.68-5.77 (m, 1H), 7.27 (d, J=8.2, 2H), 7.60 (d, J=8.0, 2H).

Step D: Trans-N-tert-butoxycarbonyl-2-(4-(amino(hydroxyimino)methyl)phenyl)-4-(2-propenyl)-pyrrolidine The title compound was prepared using a procedure analogous to that described in AMIDOXIME 1, Step H substituting trans-N-tert-butyloxycarbonyl-2-(4-cyanophenyl)-4-(2-propenyl)-pyrrolidine for methyl trans-5-(4-cyanophenyl)-2-oxo-3-pyrrolidineacetate. The crude amidoxime was used without further purification.

Amidoxime 7

Trans-5-(4-(amino(hydroxyimino)methyl)-3-methyl-phenyl)-2-oxo-3-(2-propenyl)-pyrrolidine

Step A: 5-(4-Methoxy-3-methyl-phenyl)-2-pyrrolidinone

2-Pyrrolidone-5-carboxylic acid (2.0 g, 15.5 mmol) and 2-methylanisole (2.1 mL, 17.0 mmol) were added to a mixture of 1.0 g (3.52 mmol) of phosphorous pentoxide and 6.7 mL methanesulfonic acid. The mixture was heated at 100° C. for 2 hr, cooled down to rt, and poured into a mixture of $H_2O$ and $CH_2Cl_2$. The aqueous layer was separated, and extracted with $CH_2Cl_2$ (3×20 mL). Organic layers were combined, washed with sat'd $NaHCO_3$, dried over $MgSO_4$, and concentrated. Chromatography on a Biotage 40+M cartridge using 4:1 v/v EtOAc/hexanes as the eluant afforded 1.78 g (56%) of the title compound: $^1$H NMR δ 1.88-1.97 (m, 1H), 2.21 (s, 3H), 2.35-2.54 (m, 3H), 3.81 (s, 3H), 4.66 (t, J=7.1, 1H), 6.53 (br. s, 1H), 6.79 (d, J=8.6, 1H), 7.05-7.09 (m, 2H).

Step B: N-tert-Butyloxycarbonyl-5-(4-methoxy-3-methyl-phenyl)-2-pyrrolidinone The title compound was prepared using a procedure analogous to that described in AMIDOXIME 1, Step C substituting 5-(4-methoxy-3-methyl-phenyl)-2-pyrrolidinone for 5-(4-cyanophenyl)-2-pyrrolidinone: $^1$H NMR δ 1.29 (s, 9H), 1.84-1.90 (m, 1H), 2.20 (s, 3H), 2.39-2.53 (m, 2H), 2.64-2.71 (m, 1H), 3.82 (s, 3H), 5.07 (dd, J=3.6, 8.3, 1H), 6.78 (d, J=8.3, 1H), 6.98-7.00 (m, 2H).

Step C: Trans-N-tert-butyloxycarbonyl-5-(4-methoxy-3-methyl-phenyl)-3-(2-propenyl)-2-pyrrolidinone The title compound was prepared using a procedure analogous to that described in AMIDOXIME 1, Step D substituting N-tert-butyloxycarbonyl-5-(4-methoxy-3-methyl-phenyl)-2-pyrrolidinone for trans N-tert-butyloxycarbonyl-5-(4-cyanophenyl)-3-(2-propenyl)-2-pyrrolidinone: $^1$H NMR δ 1.34 (s, 9H), 2.00-2.04 (m, 1H), 2.12-2.24 (m, 5H), 2.63-2.68 (m, 1H), 2.74-2.81 (m, 1H), 3.82 (s, 3H), 5.03-5.10 (m, 3H), 5.69-5.77 (m, 1H), 6.76 (d, J=8.3, 1H), 6.94-6.97 (m, 214).

Step D: Trans-5-(4-methoxy-3-methyl-phenyl)-3-(2-propenyl)-2-pyrrolidinone

The title compound was prepared using a procedure analogous to that described in AMIDOXIME 1, Step E substituting trans-N-tert-butyloxycarbonyl-5-(4-methoxy-3-methyl-phenyl)-3-(2-propenyl)-2-pyrrolidinone for methyl trans-N-tert-butyloxycarbonyl-5-(4-cyanophenyl)-2-oxo-3-pyrrolidineacetate: $^1$H NMR δ 2.07-2.13 (m, 1H), 2.21 (s, 3H), 2.22-2.33 (m, 211), 2.55-2.60 (m, 1H), 2.62-2.66 (m, 114), 3.82 (s, 3H), 4.61-4.63 (m, 1H), 5.06-5.14 (m, 2H), 5.77-5.82 (m, 1H), 5.99 (br. s, 1H), 6.78 (d, J=8.0, 1H), 7.03-7.06 (m, 2H).

Step E: Trans-5-(4-Hydroxy-3-methyl-phenyl)-3-(2-propenyl)-2-pyrrolidinone

Boron tribromide (10.1 mL, 1.0 M in $CH_2Cl_2$, 10.1 mmol) was added dropwise to a solution of trans-5-(4-methoxy-3-methyl-phenyl)-3-(2-propenyl)-2-pyrrolidinone (1.13 g, 4.61 mmol) in 10.0 mL of $CH_2Cl_2$ at −78° C. The mixture was stirred at −78° C. for 30 min and then at 0° C. for 1 hr. The reaction was quenched by 20 mL of $H_2O$. The mixture was poured into a mixture of ethyl ether and EtOAc (1:1, 50.0 mL) and extracted with 2.0 N of NaOH (3×30 mL). Aqueous layers were combined and acidified using 5.0 N HCl and extracted with EtOAc (3×50 mL). Organic layers were combined, dried over $MgSO_4$, and concentrated to give 940 mg (88%) of the crude title compound as a light brown solid, which was used for next step without further purification.

Step F: Trans-5-(4-trifluoromethanesulfonyloxy-3-methyl-phenyl)-3-(2-propenyl)-2-pyrrolidinone The title compound was prepared using a procedure analogous to that described in AMIDOXIME 1, Step A substituting trans-5-(4-hydroxy-3-methyl-phenyl)-3-(2-propenyl)-2-pyrrolidinone for 5-(4-hydroxyphenyl)-2-pyrrolidinone: $^1$H NMR δ 2.08-2.29 (m, 1H), 2.23-2.29 (m, 1H), 2.34-2.40 (m, 4H), 2.55-2.66 (m, 2H), 4.68-4.71 (m, 1H), 5.08-5.15 (m, 2H), 5.75-5.83 (m, 1H), 6.33 (br. s, 1H), 7.16 (dd, J=2.3, 8.5, 111), 7.21-7.24 (m, 2H).

Step G: Trans-5-(4-cyano-3-methyl-phenyl)-3-(2-propenyl)-2-pyrrolidinone

The title compound was prepared using a procedure analogous to that described in AMIDOXIME 1, Step B substituting trans-5-(4-trifluoromethanesulfonyloxy-3-methyl-phenyl)-3-(2-propenyl)-2-pyrrolidinone for 5-(4-trifluoromethanesulfonyloxyphenyl)-2-pyrrolidinone: $^1$H NMR δ 2.06-2.11 (m, 1H), 2.23-2.29 (m, 1H), 2.36-2.42 (m, 5H), 4.71-4.73 (m, 1H), 5.08-5.14 (m, 2H), 5.74-5.80 (m, 1H), 6.41 (br. s, 1H), 7.18 (d, J=8.0, 11H), 7.23 (br. s, 1H), 7.59 (d, J=7.8, 11H).

Step H: Trans-5-(4-(amino(hydroxyimino)methyl)-3-methyl-phenyl)-2-oxo-3-(2-propenyl)-pyrrolidine The title compound was prepared using a procedure analogous to that described in AMIDOXIME 1, Step H substituting trans-5-(4-cyano-3-methyl-phenyl)-3-(2-propenyl)-2-pyrrolidinone for methyl trans-5-(4-cyanophenyl)-2-oxo-3-pyrrolidineacetate. The crude amidoxime was used without further purification.

Preparation of Carboxylic Acid Intermediates

Carboxylic Acid 1

4-(4-Fluorophenyl)-5-(trifluoromethyl)thiophene-2-carboxylic acid

Step A: (E/Z)-(2-(4-Fluorophenyl)-3-chloro-4,4,4-trifluoro-2-butanal

Phosphorus oxychloride (6.8 mL, 74 mmol) was added to 25 mL of DMF at 0° C. The resulting mixture was warmed to rt and stirred for 1 hr. A solution of 1,1,1-trifluoromethyl-3-(4-fluorophenyl)-2-propanone (5.1 g, 24.8 mmol) in 10 mL of DMF was added and the resulting mixture was stirred at 70° C. for 20 hr. The reaction mixture was cooled to rt, poured onto 100 g of ice, and added sodium acetate (6.0 g). The mixture was stirred at ambient temperature for 1 hr and then extracted with ether (3×100 mL). The organic layers were combined, dried over $MgSO_4$, and concentrated. Chromatography on a Biotage 40+M cartridge using 1:19 v/v EtOAc/hexanes as the eluant afforded 4.0 g (64%) of the title compound.

Step B: Ethyl (4-(4-fluorophenyl)-5-trifluoromethyl)thiophene-2-carboxylate

To a suspension of ethyl mercaptoacetate (2.1 mL, 19.1 mmol) and sodium hydride (482 mg, 19.1 mmol) in 20 mL of THF at 0° C. was added (E/Z)-(2-(4-fluorophenyl)-3-chloro-4,4,4-trifluoro-2-butanal (4.0 g, 15.9 mmol). After stirring at rt overnight, the reaction was quenched with 50 mL of sat'd $NH_4Cl$. The mixture was partitioned between 250 mL of ether and 100 mL of water. The organic layer was separated, dried over $Na_2SO_4$, and concentrated. Chromatography on a Biotage 40+M cartridge using 1:19 v/v EtOAc/hexanes as the eluant afforded 4.4 g (86%) of the title compound: $^1$H NMR δ 1.39 (t, J=7.1, 3H), 4.39 (q, J 7.2, 2H), 7.12 (t, J=8.7, 2H), 7.39 (dd, J=5.3, 8.5, 2H), 7.70 (d, J=1.4, 1H).

Step C: 4-(4-Fluorophenyl)-5-(trifluoromethyl)thiophene-2-carboxylic acid

To a solution of ethyl (4-(4-fluorophenyl)-5-trifluoromethyl)thiophene-2-carboxylate (948 mg, 3.0 mmol) in 10 mL of EtOH was added sodium hydroxide (358 mg, 8.9 mmol). After stirring for 3 hr, solvent was removed and the residue was partitioned between diluted HCl (100 mL, pH=3) and a mixture of 1:1 v/v EtOAc:ether (200 mL). The aqueous layer was separated and further extracted with ether (2×50 mL). Organic layers were combined, dried over $Na_2SO_4$, and concentrated to give the title compound: $^1$H NMR δ 7.14 (t, J=8.5, 2H), 7.39 (dd, J=5.3, 8.5, 2H), 7.70 (d, J=1.4, 1H), 10.6 (br. s, 1H).

Carboxylic Acid 2

3-Fluoro-4-isobutylbenzoic acid

Step A: Methyl 3-fluoro-4-isobutylbenzoate

To a solution of methyl 4-bromo-3-fluorobenzoate (322 mg, 1.38 mmol) and isobutylzinc bromide (4.1 mL, 0.5 M in THF) in 10 mL of THF was added bis(tri-tert-butylphosphine)palladium(0) (14 mg, 0.03 mmol). The mixture was flushed with nitrogen three times and then stirred at rt overnight. The reaction was quenched by adding 5.0 mL of 1.0 N HCl solution and extracted with Et$_2$O (3×20 mL). Organic layers were combined, washed with brine, dried over MgSO$_4$, and concentrated. Chromatography on a Biotage 40+S cartridge using 1:99 v/v EtOAc/hexanes as the eluant afforded 243 mg (84%) of the title compound: $^1$H NMR δ 0.92 (d, J=6.6, 6H), 1.93 (m, 1H), 2.56 (d, J=6.1, 2H), 3.91 (s, 31H), 7.21 (t, J=7.6, 11H), 7.67 (dd, J=1.5, 10.2, 11H), 7.74 (dd, J=1.6, 7.8, 11H).

Step B: 3-Fluoro-4-isobutylbenzoic acid

To a solution of methyl 3-fluoro-4-isobutylbenzoate (243 mg, 1.16 mmol) in 10 mL of EtOH was added sodium hydroxide (2.3 mL, 5.0 N). The mixture was stirred at rt for 1 hr and then concentrated. The residue was partitioned in a mixture of diluted HCl (10 mL) and Et$_2$O (10 mL). The aqueous layer was separated and further extracted with Et$_2$O (2×10 mL). The organic layers were combined, dried over MgSO$_4$, and concentrated to give 212 mg (93%) of the title compound: $^1$H NMR δ 0.93 (d, J=6.6, 6H), 1.95 (m, 1H), 2.58 (d, J=7.4, 2H), 7.26 (m, 1H), 7.74 (dd, J=1.4, 10.1, 11H), 7.82 (dd, J=1.5, 7.9, 11H), 11.2 (br. s, 1H).

Carboxylic Acid 3

3-Fluoro-4-(3-methylbutyl)benzoic acid

The title compound was prepared using procedures analogous to those described for CARBOXYLIC ACID 2 substituting 3-methylbutylzinc bromide for isobutylzinc bromide in Step A: $^1$H NMR δ 0.95 (d, J=6.4, 6H), 1.51 (m, 2H), 1.52 (m, 1H), 2.70 (t, J 8.0, 2H), 7.30 (1, J=7.6, 1H), 7.72 (dd, J=1.3, 10.2, 11H), 7.82 (dd, J=1.4, 7.8, 11H).

Carboxylic Acid 4

4-((R)-3,3-difluorocyclopentyl)benzoic acid

Step A: (3R)-3-(4-Bromophenyl)cyclopentanone

To a mixture of 7.2 g (35.8 mmol) of 4-bromophenylboronic acid, 186 mg (0.72 mmol) of acetylacetonatobis(ethylene)rhodium (I) and 446 mg (0.71 mmol) of (R)-2,2'-bis(diphenylphosphino)-1,1'binaphthyl (BINAP) in 60 mL of dioxane and 6 mL of H$_2$O under nitrogen was added 1.0 mL (11.9 mmol) of 2-cyclopenten-1-one. After refluxing for 5.5 h, the reaction was concentrated. The residue was partitioned between 300 mL of EtOAc and 300 mL of 1 N NaHCO$_3$. After separating phases, the organic layer was washed with 300 mL of brine, dried over Na$_2$SO$_4$ and concentrated. The residue was purified on a 40M Biotage column using 9:1 v/v hexane/EtOAc as the eluant to afford 1.90 g of the title compound as a white solid: $^1$H NMR δ 1.97 (m, 1H), 2.29-2.37 (m, 2H), 2.43-2.52 (m, 2H), 2.69 (m, 1H), 3.40 (m, 1H), 7.16 (d, J=8.5, 2H), 7.49 (d, J=8.5, 2H).

Step B:
(R)-3-(4-Bromophenyl)-1,1-difluorocyclopentane

A mixture of 2.1 mL (11.4 mmol) of [bis(2-methoxyethyl)amino]sulfur trifluoride and 0.10 mL (0.7 mmol) of boron trifluoride etherate in 7 mL of toluene at 0° C. was allowed to stand for 1.3 h with occasional stirring. A solution of 1.9 g (7.9 mmol) of (R)-3-(4-bromophenyl)cyclopentanone (from Step A) in 13 mL of toluene was added. The reaction was stirred at 55° C. for 2 days. After cooling, the mixture was added to 250 mL of 2N NaOH and 250 mL of Et$_2$O at 0° C. After stirring for 30 min, the phases were separated. The organic layer was washed with 250 mL of 1 N NaOH and 250 mL of H$_2$O, dried over MgSO$_4$ and concentrated. The residue was purified on a 40M Biotage column using 49:1 v/v hexane/Et$_2$O as the eluant to afford 1.47 g of the title compound: $^1$H NMR δ 1.85 (m, 1H), 2.09-2.26 (m, 3H), 2.35 (m, 1H), 2.56 (m, 1H), 3.30 (m, 1H), 7.13 (d, J=8.3, 2H), 7.46 (d, J=8.3, 2H).

Step C: 4-((R)-3,3-Difluorocyclopentyl)benzoic acid

A solution of 1.0 g (3.8 mmol) of (R)-3-(4-bromophenyl)-1,1-difluorocyclopentane (from Step B) in 15 mL of THF at −78° C. was treated with 1.6 mL (4.0 mmol) of 2.5M BuLi in hexanes. After stirring for 15 min, the reaction mixture was added to a suspension of dry ice in 200 mL of Et$_2$O. The mixture was allowed to warm to rt. The reaction mixture was extracted with 100 mL of 1 N NaOH. After separating phases, the aqueous layer was acidified to pH 1-2 with concentrated HCl. The aqueous phase was extracted with 3×100 mL of CH$_2$Cl$_2$. The combined organic phases were dried and concentrated to give 0.67 g of the title compound: $^1$H NMR (CD$_3$OD) δ 1.87 (m, 1H), 2.13-2.37 (m, 4H), 2.54 (m, 11H), 3.41 (m, 1H), 7.39 (d, J=8.2, 2H), 7.97 (d, J=8.2, 2H).

Carboxylic Acid 5

4-((S)-3,3-difluorocyclopentyl)benzoic acid

The title compound was prepared using analogous procedures analogous to that of CARBOXYLIC ACID 4 substituting (S)-2,2'-bis(diphenylphosphino)-1,1'binaphthyl (BINAP) for (R)-2,2'-bis(diphenylphosphino)-1,1'binaphthyl (BINAP) in Step A: $^1$H NMR (CD$_3$OD) δ 1.87 (m, 1H), 2.13-2.37 (m, 4H), 2.54 (m, 1H), 3.41 (m, 1H), 7.39 (d, J=8.2, 2H), 7.97 (d, J 8.2, 2H).

Carboxylic Acid 6

4-((R)-3,3-difluorocyclohexyl)benzoic acid

The title compound was prepared using analogous procedures analogous to that of CARBOXYLIC ACID 4 substituting 2-cyclohexen-1-one for 2-cyclopenten-1-one in Step A: $^1$H NMR δ 1.47 (m, 1H), 1.66-1.96 (m, 5H), 2.19 (m, 1H), 2.31 (m, 1H), 2.96 (m, 1H), 7.32 (d, J=8.3, 2H), 8.07 (d, J=8.2, 2H).

Carboxylic Acid 7

4-((S)-3,3-difluorocyclohexyl)benzoic acid

The title compound was prepared using analogous procedures analogous to that of CARBOXYLIC ACID 6 substituting (S)-2,2'-bis(diphenylphosphino)-1,1'binaphthyl (BINAP) for (R)-2,2'-bis(diphenylphosphino)-1,1'binaphthyl (BINAP): $^1$H NMR δ 1.47 (m, 1H), 1.66-1.96 (m, 5H), 2.19 (m, 1H), 2.31 (m, 1H), 2.96 (m, 114), 7.32 (d, J=8.3, 2H), 8.07 (d, J=8.2, 2H).

Carboxylic Acid 8

4-((1R,3R)-3-fluorocyclopentyl)benzoic acid

Step A: (3S)-3-(4-bromophenyl)cyclopentanol

To a solution of (3R)-3-(4-Bromophenyl)cyclopentanone (1.14 g, 4.77 mmol, CARBOXYLIC ACID 4, Step A) in 10 mL of $CH_2Cl_2$ at –78° C. was added diisobutylaluminum hydride (7.2 mL, 1.0 M in $CH_2Cl_2$). The mixture was stirred at –78° C. for 1 hr and then 5.0 mL of sat'd Rochelle's salt aqueous solution was added. The mixture was poured into diluted HCl solution and extracted with $CH_2Cl_2$ (3×10 mL). Organic layers were combined, washed with sat'd $NaHCO_3$ and brine. The organic layer was dried over $MgSO_4$ and concentrated to give 1.16 g (100%) of the title compound as a 1:1 ratio diastereomeric mixture, which cannot be separated by chromatography.

Step B: (1R,3R)-3-(4-bromophenyl)cyclopentyl acetate and (1S,3R)-3-(4-bromophenyl)cyclopentanol A suspension of (3S)-3-(4-bromophenyl)cyclopentanol (1.01 g, 4.19 mmol) and Porcine Pancreas Lipase (PPL, 1.0 g, Sigma) in 20.0 mL of 1:1 v/v vinyl acetate/hexanes was stirred at rt overnight. Enzyme was filtered off through a cake of Celite and washed with EtOAc and hexanes. The filtrate was concentrated. Chromatography on a Biotage 40+M cartridge using 1:19 v/v EtOAc/hexanes as the eluant afforded 536 mg (45%) of (1R,3R)-3-(4-bromophenyl)cyclopentyl acetate: $^1$H NMR δ 1.59 (m, 1H), 1.77-1.89 (m, 2H), 2.05 (s, 3H), 2.12-2.29 (m, 3H), 3.25 (m, 1H), 5.30 (m, 1H), 7.09 (d, J=8.2, 2H), 7.41 (d, J=8.3, 2H), and using 1:3 v/v EtOAc/hexanes as the eluant gave 503 mg (50%) of (1S,3R)-3-(4-bromophenyl)cyclopentanol: $^1$H NMR δ1.61 (m, 2H), 1.77-1.94 (m, 311), 2.04 (m, 1H), 2.45 (m, 1H), 3.01 (m, 1H), 4.45 (m, 1H), 7.16 (d, J=8.3, 2H), 7.40 (d, J=8.5, 2H).

Step C: 1-Bromo-4-((1R,3R)-3-fluorocyclopentyl)benzene

To a solution of (1S,3R)-3-(4-bromophenyl)cyclopentanol (503 mg, 2.09 mmol) in 10 mL of $CH_2Cl_2$ at –78° C. was added (bis(2-methoxyethyl)amino)sulfur trifluoride (Deoxo-Fluor, 462 µL, 2.50 mmol). The mixture was allowed to gradually warm up to rt overnight and then poured into sat'd $NaHCO_3$ (20 mL). The aqueous layer was extracted with $CH_2Cl_2$ (3×20 mL). The organic layer was dried over $MgSO_4$ and concentrated. Chromatography on a Biotage 40+S cartridge using hexanes as the eluant afforded 383 mg (76%) of the title compound: $^1$H NMR δ 1.53-1.78 (m, 2H), 1.95-2.39 (m, 4H), 3.35 (m, 1H), 5.19-5.32 (m, 1H), 7.09 (d, J 8.5, 2H), 7.40 (d, J=8.2, 2H).

Step D: 4-((1R,3R)-3-fluorocyclopentyl)benzoic acid

The title compound was prepared using a procedure analogous to that described for CARBOXYLIC ACID 4 substituting 1-bromo-4-((1R,3R)-3-fluorocyclopentyl)benzene for 1-bromo-4-((1R)-3,3-difluorocyclopentyl)benzene in Step D: $^1$H NMR δ 1.65-1.87 (m, 2H), 1.99-2.46 (m, 4H), 3.47 (m, 1H), 5.23-5.36 (m, 1H), 7.33 (d, J=8.2, 2H), 8.05 (d, J=8.2, 2H).

Carboxylic Acid 9

4-((1R,3S)-3-fluorocyclopentyl)benzoic acid

Step A: (1R,3R)-3-(4-Bromophenyl)cyclopentanol

To a solution of (1R,3R)-3-(4-bromophenyl)cyclopentyl acetate (CARBOXYLIC ACID 8, Step B, 536 mg, 1.9 mmol) in 5.0 mL of EtOH was added sodium hydroxide (1.9 mL, 5.0 N). After stirring at rt for 30 min, solvent was removed and the residue was partitioned between sat'd $NaHCO_3$ (50 mL) and $CH_2Cl_2$ (50 mL). The aqueous layer was separated and extracted with $CH_2Cl_2$ (2×50 mL). Organic layers were combined, dried over $MgSO_4$, and concentrated. Chromatography on a Biotage 40+M cartridge using 7:3 v/v hexanes/EtOAc as the eluant afforded 445 mg (97%) of the title compound: $^1$H NMR δ 1.49 (br. s, 1H), 1.56-1.81 (m, 2H), 2.05-2.27 (m, 4H), 3.35 (m, 1H), 4.52 (m, 1H), 7.09 (d, J=8.2, 2H), 7.40 (d, J=8.3, 2H).

Step B: 4-((1R,3S)-3-Fluorocyclopentyl)benzoic acid

The title compound was prepared using a procedure analogous to that described for CARBOXYLIC ACID 8 substituting (1R,3R)-3-(4-bromophenyl)cyclopentanol for (1S,3R)-3-(4-bromophenyl)cyclopentanol in Step C.

Carboxylic Acid 10

3-Fluoro-4-cyclopentylbenzoic acid

A solution of 0.45 g (1.45 mmol) of benzyl 3-fluoro-4-bromobenzoate (0.45 g, 1.45 mmol) in 4.4 mL of 0.5 M cyclopentylzinc bromide solution in THF was treated with ~5 mg of bis(tri-t-butylphosphine)palladium(0) and the resulting mixture was stirred at rt for 24 h. The reaction mixture was directly purified on a Biotage 40S cartridge using 1:1 hexanes/EtOAc as the eluant. A mixture of the resulting solid (0.27 g, 0.91 mmol) and 10% Pd/C in 5 mL of MeOH was stirred under 1 atm of $H_2$ for 3 h. The reaction was filtered and concentrated. Purification by HPLC B afforded the title compound: $^1$H NMR δ 1.58-1.90 (m, 6H), 2.05-2.14 (m, 2H), 3.30 (m, 1H), 7.36 (t, J=7.7, 1H), 7.72 (dd, J=1.6, 10.5, 1H), 7.83 (dd, J=1.6, 8.0, 1H).

Carboxylic Acid 11

2-Fluoro-4-cyclopentylbenzoic acid

The title compound was prepared using a procedure analogous to that described for CARBOXYLIC ACID 10 substituting benzyl 2-fluoro-4-bromobenzoate for benzyl 3-fluoro-4-bromobenzoate: $^1$H NMR δ 1.57-1.85 (m, 6H), 2.07-2.13 (m, 2H), 3.05 (m, 1H), 7.03 (dd, J 1.1, 12.4, 1H), 7.10 (dd, J=1.4, 8.2, 11H), 7.94 (t, J=8.0, 11H).

Carboxylic Acid 12

3-Trifluoromethyl-4-(((1S)-1-methylpropyl)oxy) benzoic acid

Step A: 3-Trifluoromethyl-4-(2-(S)-butoxy)benzonitrile

A solution of 1.1 g (5.9 mmol) of 4-fluoro-3-trifluoromethylbenzonitrile and 485 mg (6.5 mmol) of (S)-(+)-2-butanol in 10 mL of THF at –10° C. was treated with 235 mg (5.9 mmol) of sodium hydride. The resulting mixture was stirred at cold for 2 h, then quenched with 10 mL of $H_2O$. The quenched solution was extracted with 30 mL of Et$_2$O, dried over MgSO$_4$ and concentrated. Chromatography on a Biotage 40M cartridge using 4:1 v/v hexanes/Ethyl acetate as the eluant afforded 550 mg of the title compound: $^1$H NMR δ 0.99 (t, J=7.6, 3H), 1.35 (d, J=6.2, 3H), 1.58-1.83 (m, 2H), 4.51 (septet, 1H), 7.04 (d, J=8.7, 1H), 7.75 (d, J=8.7, 1H), 7.85 (s, 1H).

Step B: 3-Trifluoromethyl-4-(2-(S)-butoxy)benzoic acid

A solution of 550 mg (2.2 mmol) of 3-trifluoromethyl-4-(2-(S)-methylpropyloxy)benzonitrile (from Step A) in 5 mL of ethanol was treated with 1.5 mL of 5.0 N NaOH and was heated to 80° C. for 3 h. The reaction was then concentrated, treated with 2 N HCl, extracted with 30 mL of EtOAc, dried and concentrated to afford 600 mg of the title compound: $^1$H NMR δ 0.99 (t, J=7.3, 3H), 1.43 (d, J=5.9, 3H), 1.73-1.83 (m, 2H), 4.54 (septet, 1H), 7.02 (d, J=8.9, 1H), 8.21 (d, J=8.9, 1H), 8.32 (s, 1H).

Carboxylic Acid 13

3-Chloro-4-isopropoxybenzoic acid

Step A: Methyl 3-chloro-4-isopropoxybenzoate

To a solution of 1.42 g (7.63 mmol) of methyl 3-chloro-4-hydroxybenzoate, 585 μL (7.63 mmol) of 2-propanol, and 3.0 g (11.45 mmol) of triphenylphosphine in 20 mL of THF at 0° C. was added 2.25 mL (11.45 mmol) of diisopropyl azodicarboxylate. The mixture was allowed to warm up to rt and stirred for 16 hr. The solvent was removed. Chromatography on a Biotage 40+M cartridge using 1:19 v/v EtOAc/hexanes as the eluant afforded 1.77 g (100%) of the title compound: $^1$H NMR δ 1.41 (d, J=6.2, 6H), 4.63-4.70 (m, 1H), 6.93 (d, J=8.7, 1H), 7.89 (dd, J=2.2, 8.6, 1H), 8.05 (d, J=2.0, 1H).

Step B: 3-Chloro-4-isopropoxybenzoic acid

The title compound was prepared using procedure analogous to that described for CARBOXYLIC ACID 2 substituting methyl 3-cyano-4-isopropoxybenzoate for methyl 3-fluoro-4-isobutylbenzoate in Step B: $^1$H NMR δ 1.43 (d, J=5.9, 6H), 4.66-4.73 (m, 11H), 6.96 (d, J=8.9, 1H), 7.97 (dd, J=2.1, 8.7, 1H), 8.12 (d, J=2.0, 1H), 11.7 (br. s, 11H).

Carboxylic Acids 14-15

The following carboxylic acid intermediates were prepared using procedures analogous to those described for CARBOXYLIC ACID 13 substituting the appropriate alcohol for 2-propanol in Step A.

| ACID | R | $^1$H NMR δ |
|---|---|---|
| 14 | cyclopentyl-O- | 1.67 (m, 2H), 1.84-1.97 (m, 6H), 4.90 (m, 1H), 6.96 (d, J = 8.7, 1H), 7.96 (dd, J = 1.8, 8.7, 1H), 8.11 (d, J = 2.1, 1H) |
| 15 | isobutyl-O- | 1.08 (d, J = 6.8, 6H), 2.18 (m, 1H), 3.85 (d, J = 6.6, 2H), 6.92 (d, J = 8.7, 1H), 7.97 (dd, J = 2.0, 8.7, 1H), 8.11 (d, J = 2.1, 1H) |

Carboxylic Acid 16

4-(4,4-Difluorocyclohexyl)benzoic acid

Step A: 1,4-Dioxaspiro[4.5]dec-7-en-8-yl trifluoromethanesulfonate

To a solution of lithium N,N-diisopropylamide (30.6 mmol) in 30 mL of THF at −78° C. was added a solution of 1,4-dioxaspiro[4.5]decan-8-one (4.06 g, 26.0 mmol) in 15 mL of THF dropwise. The resulting mixture was stirred at −78° C. for 25 min, to which a solution of 2-(N,N-bis(trifluoromethylsulfonyl)amino)-5-chloropyridine (12.0 g, 30.5 mmol) in 15 mL of THF was then added dropwise. After stirring at −78° C. for 2.5 h, the reaction was quenched by adding 10 mL of 1 N aqueous solution of NaHCO$_3$. The mixture was partitioned between Et$_2$O (200 mL) and 1 N NaHCO$_3$ (200 mL). The organic layer was separated, dried over MgSO$_4$, and concentrated. Chromatography on a Biotage 40M cartridge using 1:9 v/v EtOAc/hexanes as the eluant afforded 4.62 g (61%) of the title compound.

Step B: 4-(1,4-Dioxaspiro[4.5]dec-7-en-8-yl)benzoic acid

To a solution of 4-carboxyphenylboronic acid (0.69 g, 3.53 mmol) and 1,4-dioxaspiro[4.5]dec-7-en-8-yl trifluoromethanesulfonate (1.02 g, 3.53 mmol) in 14 mL of DMF were added 7 mL of 2 N aqueous solution of Na$_2$CO$_3$, triphenylphosphine (159 mg, 0.61 mmol), and tris(dibenzylideneacetone)dipalladium(0) (68 mg, 74.2 μmol). After stirring at 80° C. for 3 h and then at rt for 16 h, the mixture was concentrated and partitioned between 100 mL of Et$_2$O and 150 mL of H$_2$O. The aqueous layer was separated and acidified to pH ~2-3 using concentrated HCl, and extracted with CH$_2$Cl$_2$ (2×100 mL). The organic layers were combined, dried over Na$_2$SO$_4$, and concentrated. The residue was recrystallized from 10 mL of EtOAc to give 353 mg (38%) of the title compound.

Step C: Methyl 4-(1,4-dioxaspiro[4.5]dec-7-en-8-yl)benzoate

A mixture of 4-(1,4-dioxaspiro[4.5]dec-7-en-8-yl)benzoic acid (572 mg, 2.20 mmol), iodomethane (140 μL, 2.24 mmol), and cesium carbonate (710 mg, 2.17 mmol) in 6 mL of DMF was stirred at rt for 16 h. The mixture was diluted with H$_2$O (10 mL) and extracted with Et$_2$O (100 mL). The organic layer was separated, dried over MgSO$_4$, and concentrated. Chromatography on a Biotage 40S cartridge using 3:17 v/v EtOAc/hexanes as the eluant afforded 399 mg (72%) of the title compound.

Step D: Methyl 4-(1,4-dioxaspiro[4.5]dec-8-yl)benzoate

A mixture of methyl 4-(1,4-dioxaspiro[4.5]dec-7-en-8-yl) benzoate (514 mg, 1.87 mmol) and 10% Pd/C (127 mg) in 15 mL of 1:2 v/v EtOAc/CH$_3$OH was shaken for 6.5 h under 45 Psi of H$_2$ using a Parr shaker. Catalyst was filtered off through a cake of Celite and washed with copious of EtOAc. The filtrate was concentrated to give 480 mg of the title compound.

Step E: Methyl 4-(4-oxocyclohexyl)benzoate

To a solution of methyl 4-(1,4-dioxaspiro[4.5]dec-8-yl) benzoate (480 mg, 1.73 mmol) in 8 mL of THF was added 4 mL of 1 N of aqueous HCl solution. The mixture was stirred at rt for 21 h and concentrated. The residue was partitioned between 50 mL of Et$_2$O and 50 mL of 1 N aqueous NaHCO$_3$ solution. The organic layer was separated, dried over MgSO$_4$, and concentrated. Chromatography on a Biotage 40S cartridge using 1:9 v/v EtOAc/hexanes as the eluant afforded 343 mg (85%) of the title compound.

Step F: Methyl 4-(4,4-difluorocyclohexyl)benzoate

The title compound was prepared using procedure analogous to that described for CARBOXYLIC ACID 4 substituting methyl 4-(4-oxocyclohexyl)benzoate for (3R)-3-(4-bromophenyl)cyclopentanone in Step B.

Step G: 4-(4,4-Difluorocyclohexyl)benzoic acid

The title compound was prepared using procedure analogous to that described for CARBOXYLIC ACID 1 substituting methyl 4-(4,4-difluorocyclohexyl)benzoate for ethyl (4-(4-fluorophenyl)-5-trifluoromethyl)thiophene-2-carboxylate in Step C: $^1$H NMR (CD$_3$OD) δ 1.82 (m, 2H), 1.94 (m, 4H), 2.16 (m, 2H), 2.78 (m, 1H), 7.36 (d, J=8.2, 2H), 7.96 (d, J=8.2, 2H).

Preparation of Examples

Example 1

Trans-2-(4-(5-(4-(2-methylpropyl)phenyl)-1,2,4-oxadiazol-3-yl)phenyl)-4-pyrrolidineacetic acid

Step A: Methyl trans-5-(4-(5-(4-(2-methylpropyl) phenyl)-1,2,4-oxadiazol-3-yl)phenyl)-2-oxo-3-pyrrolidineacetate A solution of AMIDOXIME 1,4-(2-methylpropyl)benzoic acid (127 mg, 0.71 mmol), 1-(3-dimethylaminopropyl)-3-ethylcarbodiimide hydrochloride (149 mg, 0.78 mmol), and 1-hydroxybenzotriazole hydrate (44 mg, 0.32 mmol) in acetonitrile (10 mL) was stirred at rt for 1 hr. The mixture was concentrated, and chromatography on a Biotage 40+S cartridge using EtOAc as the eluant gave an ester intermediate.

A solution of the aforementioned ester in xylenes (10 mL) was refluxed for 2 hr and then concentrated. Chromatography on a Biotage 40+S cartridge using 3:2 v/v EtOAc/hexanes as the eluant afforded 63 mg (22% over three steps) of the title compound as a white solid: $^1$H NMR δ 0.94 (d, J=6.7, 6H), 1.92-1.97 (m, 1H), 2.33-2.59 (m, 5H), 2.89 (dd, J=4.0, 16.9, 1H), 2.97-3.00 (m, 1H), 3.70 (s, 3H), 4.85 (dd, J=3.0, 8.7, 1H), 6.08 (br. s, 1H), 7.33 (d, J=8.2, 2H), 7.42 (d, J=8.2, 2H), 8.12 (d, J=8.2, 2H), 8.18 (d, J=8.3, 2H).

Step B: Trans-2-(4-(5-(4-(2-methylpropyl)phenyl)-1, 2,4-oxadiazol-3-yl)phenyl)-4-pyrrolidineacetic acid A solution of the aforementioned lactam (63 mg, 0.15 mmol) and trimethyloxonium tetrafluoroborate (26 mg, 0.17 mmol) in CH$_2$Cl$_2$ (10 mL) was stirred at rt overnight. The reaction mixture was then washed with sat'd NaHCO$_3$ (20 mL). The aqueous layer was separated and extracted with CH$_2$Cl$_2$ (3×20 mL). Organic layers were combined, dried over MgSO$_4$, and concentrated to give an iminoether, which was used in the next step without further purification.

A solution of sodium cyanoborohydride (1.0 M in THF, 727 μL, 0.73 mmol) was added to a solution of the resulting imino ether and a bit of bromocresol green in CH$_3$OH (10 mL). A solution of HCl in 1,4-dioxane (2.0 M) was added to the reaction mixture to maintain the color was yellow (pH ~3-4), and the resulting mixture was stirred at rt for 4 hr. The mixture was then poured into sat'd NaHCO$_3$ (20 mL) and CH$_2$Cl$_2$ (20 mL), and the aqueous layer was further extracted with CH$_2$Cl$_2$ (3×20 mL). Organic layers were combined, dried over Na$_2$SO$_4$, and concentrated to give the crude amine (70 mg).

Sodium hydroxide (5.0 N, 110 μL) was added to a solution of the crude amine (23 mg, 0.05 mmol) in EtOH (5.0 mL) was stirred at room temperature for 30 min. The reaction mixture concentrated and the residue was purified on HPLC to give EXAMPLE 1 (9.7 mg, 44%): $^1$H NMR (CD$_3$OD) δ 0.88 (s, 6H), 1.86-1.91 (m, 11H), 2.23-2.29 (m, 11H), 2.44-2.64 (m, 5H), 2.93-2.99 (m, 1H), 3.12 (dd, J=7.9, 11.8, 11H), 3.70 (dd, J=7.6, 11.8, 11H), 4.85 (t, J=8.6, 11H), 7.35 (d, J=8.3, 2H), 7.60 (d, J=8.5, 2H), 8.06 (d, J=8.5, 2H), 8.18 (d, J=8.5, 2H).

Example 2

Cis-2-(4-(5-(4-(2-methylpropyl)phenyl)-1,2,4-oxadiazol-3-yl)phenyl)-4-pyrrolidineacetic acid EXAMPLE 2 was prepared using a procedure analogous to that described in EXAMPLE 1 substituting AMIDOXIME 2 for AMIDOXIME 1 in Step A: 11H NMR (CD$_3$OD) δ 1.38 (s, 9H), 2.07 (q, J=12.3, 23.8, 1H), 2.61-2.74 (m, 3H), 2.89-3.00 (m, 1H), 3.23-3.27 (m, 1H), 3.72-3.76 (m, 11H), 4.79-4.83 (m, 1H), 7.66 (d, J=8.5, 2H), 7.69 (d, J=8.5, 2H), 8.14 (d, J=8.5, 2H), 8.23 (d, J=8.5, 2H).

Example 3

Trans-1-methyl-2-(4-(5-(4-(2-methylpropyl)phenyl)-1,2,4-oxadiazol-3-yl)phenyl)-4-pyrrolidineacetic acid A mixture of methyl trans-2-(4-(5-(4-(2-methylpropyl) phenyl)-1,2,4-oxadiazol-3-yl)phenyl)-4-pyrrolidineacetate (EXAMPLE 1, Step B, 18 mg, 0.04 mmol), iodomethane (3 μL, 0.05 mmol), and potassium carbonate (30 mg, 0.21 mmol) in 2.0 mL of DMF was stirred at 100° C. for 1 h. After cooled down to rt, the reaction mixture was filtered through a cake of Celite and the residue was washed with CH$_2$Cl$_2$ (50 mL). The filtrate was washed with brine and dried over Na$_2$SO$_4$ and concentrated to give the crude amine.

To a solution of the aforementioned crude amine in EtOH (4.0 mL) was added NaOH (86 μL of 5.0 N NaOH, 0.43 mmol). After stirring at rt for 16 h, the reaction mixture was concentrated. Chromatography on a Biotage 40+S cartridge using 3:17 v/v CH$_3$OH/CH$_2$Cl$_2$ having 1.0% NH$_4$OH as the eluant afforded 8.0 mg (44% over two steps) of the title compound as a white solid: 111 NMR δ 0.88 (d, J=6.7, 611), 1.88 (m, 1H), 2.28 (m, 1H), 2.52-2.61 (m, 5H), 2.69 (s, 3H), 2.99 (m, 2H), 3.91 (dd, J=6.9, 10.8, 11H), 4.43 (t, J=9.1, 11H), 7.36 (d, J=8.2, 2H), 7.63 (d, J=8.2, 2H), 8.07 (d, J=8.2, 2H), 8.21 (d, J=8.5, 2H).

Example 4

Trans-2-(4-(5-(4-(4-fluorophenyl)-5-trifluoromethyl-2-thienyl)-1,2,4-oxadiazol-3-yl)phenyl)-4-pyrrolidineacetic acid Step A: Trans-3-allyl-5-(4-(5-(4-(4-fluorophenyl)-5-trifluoromethyl-2-thienyl)-1,2,4-oxadiazol-3-yl)phenyl)pyrrolidin-2-one The title compound was prepared using a procedure analogous to that described in EXAMPLE 1 substituting AMIDOXIME 3 for AMIDOXIME 1 and 4-(4-fluorophenyl)-5-(trifluoromethyl)thiophene-2-carboxylic acid for 4-(2-methylpropyl)benzoic acid, respectively, in Step A: $^1$H NMR (CD$_3$OD) δ 2.16 (m, 1H), 2.28 (m, 1H), 2.42 (m, 1H), 2.63 (m, 2H), 4.79 (m, 1H), 5.12 (m, 2H), 5.80 (m, 1H), 6.01 (s, 1H), 7.17 (t, J=8.7, 2H), 7.44 (m, 4H), 7.88 (m, 1H), 8.14 (d, J=8.4, 2H).

Step B: Methyl trans-2-(4-(5-(4-(4-fluorophenyl)-5-trifluoromethyl-2-thienyl)-1,2,4-oxadiazol-3-yl)phenyl)-4-pyrrolidineacetate Ruthenium(III) chloride hydrate (1 mg, 4.4 μmol) was added into a solution of trans 3-allyl-5-(4-(5-(4-(4-fluorophenyl)-5-trifluoromethyl-2-thienyl)-1,2,4-oxadiazol-3-yl)phenyl)pyrrolidin-2-one (103 mg, 0.20 mmol) and sodium periodate (193 mg, 0.90 mmol) in a mixed solvent (7.0 mL) of 2:2:3 v/v/v CCl$_4$/CH$_3$CN/H$_2$O. The mixture was stirred at rt for 1 hr and then partitioned between H$_2$O (20 mL) and CH$_2$Cl$_2$ (20 mL). The aqueous layer was separated and extracted with CH$_2$Cl$_2$ (3×20 mL). Organic layers were combined, dried over Na$_2$SO$_4$, and concentrated to give the crude acid as a colorless syrup.

(Trimethylsilyl)diazomethane (2.0 M in hexanes, 48 μL, 0.10 mmol) was added to a solution of the crude acid in a mixed solvent (9 mL) of 7:2 v/v benzene/CH$_3$OH. After 30 min, the reaction mixture was concentrated. Chromatography on a Biotage 40+S cartridge using 3:2 v/v EtOAc/hexanes as the eluant afforded 20.0 mg (18% over two steps) of the title compound as a white solid: $^1$H NMR δ 2.36 (m, 1H), 2.44-2.58 (m, 2H), 2.90 (dd, J=4.0, 7.0, 1H), 2.98 (m, 11H), 3.71 (s, 3H), 4.85 (dd, J=2.9, 9.0, 1H), 5.89 (s, 1H), 7.17 (d, J=8.6, 2H), 7.42-7.47 (m. 4H), 7.89 (m, 1H), 8.15 (d, J=8.2, 2H).

Step C: Trans-2-(4-(5-(4-(4-fluorophenyl)-5-trifluoromethyl-2-thienyl)-1,2,4-oxadiazol-3-yl)phenyl)-4-pyrrolidineacetic acid A solution of methyl trans-2-(4-(5-(4-(4-fluorophenyl)-5-trifluoromethyl-2-thienyl)-1,2,4-oxadiazol-3-yl)phenyl)-4-pyrrolidineacetate (20 mg, 0.04 mmol) and trimethyloxonium tetrafluoroborate (6.5 mg, 0.04 mmol) in 5 mL of CH$_2$Cl$_2$ was stirred at rt overnight. The mixture was washed with 20 mL of sat'd NaHCO$_3$, and the aqueous layer was extracted with CH$_2$Cl$_2$ (3×20 mL). The organic layers were combined, dried over Na$_2$SO$_4$, and concentrated to give an iminoether, which was used in next step without further purification.

A solution of sodium cyanoborohydride (1.0 M in THF, 367 μL, 0.37 mmol) was added to a solution of the aforementioned iminoether and a bit of bromocresol green in CH$_3$OH (10 mL). A solution of HCl in 1,4-dioxane (2.0 M) was added to the reaction mixture to maintain the color of the mixture as yellow. The resulting mixture was stirred at rt for 4 hr. Poured into sat'd NaHCO$_3$ and CH$_2$Cl$_2$ and the aqueous layer was further extracted with CH$_2$Cl$_2$ (3×20 mL). Organic layers were combined, dried over Na$_2$SO$_4$, and concentrated to give the crude amine, which was taken onto next step without further purification.

Sodium hydroxide (5.0 N, 94 μL) was added to a solution of the aforementioned amine in EtOH (4.0 mL) was stirred at rt for overnight. The reaction mixture was directly purified on HPLC to give the title compound (11 mg, 58% over 3 steps): $^1$H NMR (CD$_3$OD) δ 2.26 (m, 1H), 2.49 (m, 1H), 2.61 (m, 1H), 2.96 (m, 1H), 3.13 (m, 1H), 3.71 (dd, J=7.7, 11.8, 1H), 4.85 (t, J=8-6, 1H), 7.16-7.20 (m, 2H), 7.46-7.50 (m, 2H), 7.61 (d, J=8.4, 2H), 8.00 (m, 1H), 8.18 (d, J=8.2, 2H).

Example 5

Trans-2-(4-(5-(4-cyclopentylphenyl)-1,2,4-oxadiazol-3-yl)phenyl)-4-pyrrolidineacetic acid Step A: Methyl trans-N-tert-butyloxycarbonyl-2-(4-(5-(4-cyclopentylphenyl)-1,2,4-oxadiazol-3-yl)phenyl)-4-pyrrolidineacetate The title compound was prepared using a procedure analogous to that described in EXAMPLE 1 substituting AMIDOXIME 4 for AMIDOXIME 1 and 4-cyclopentylbenzoic acid for 4-(2-methylpropyl)benzoic acid, respectively, in Step A: $^1$H NMR δ 1.21 (s, 9H), 1.47-1.87 (m, 6H), 2.05-2.15 (m, 3H), 2.41-2.48 (m, 2H), 2.70 (m, 1H), 3.06-3.31 (m, 2H), 3.67 (s, 3H), 3.93 (m, 1H), 4.91 (m, 1H), 5.07 (m, 1H), 7.30 (d, J=8.0, 2H), 7.41 (d, J=8.3, 2H), 8.12 (m, 4H).

Step B: Trans-2-(4-(5-(4-cyclopentylphenyl)-1,2,4-oxadiazol-3-yl)phenyl)-4-pyrrolidineacetic acid A solution of methyl trans-N-tert-butyloxycarbonyl-2-(4-(5-(4-cyclopentylphenyl)-1,2,4-oxadiazol-3-yl)phenyl)-4-pyrrolidineacetate (4.4 mg, 8.3 μmol) in 2.5 mL of 20% TFA in CH$_2$Cl$_2$ was stirred at rt for 1 hr and then concentrated. The residue was redissolved in 5.0 mL of EtOH and sodium hydroxide (189 μL, 5.0 N, 0.95 mmol) was added. After stirring at rt for 1 hr, the reaction mixture was concentrated and the residue was purified on HPLC to give 3.5 mg (100%) of the title compound: $^1$H NMR (CD$_3$OD) δ 1.60 (m, 214), 1.69 (m, 2H), 1.81 (m, 2H), 2.06 (m, 2H), 2.26 (m, 1H), 2.46 (m, 1H), 2.58 (m, 2H), 2.96 (m, 1H), 3.07 (m, 1H), 3.12 (dd, J=7.7, 11.9, 1H), 3.70 (dd, J=7.7, 11.8, 1H), 4.84 (t, J=8.6, 1H), 7.44 (d, J=8.2, 2H), 7.60 (d, J=8.4, 2H), 8.06 (d, J=8.4, 2H), 8.18 (d, J=8.2, 2H).

Examples 6-19

The following examples were prepared using procedures analogous to those described in EXAMPLE 5 substituting the appropriate carboxylic acids for 4-(2-methylpropyl)benzoic acid in Step A. The precursors of EXAMPLES 9 and 10-products in EXAMPLE 5, Step A—were separated on Chiralcel OD 20×250 mm column with isocratic 85:15 v/v heptane/EtOH over 30 min, flow rate at 8.0 mL/min, and UV wavelength at 254 nm. The precursor of EXAMPLE 9 has a shorter retention time under this separation condition than does that of EXAMPLE 10.

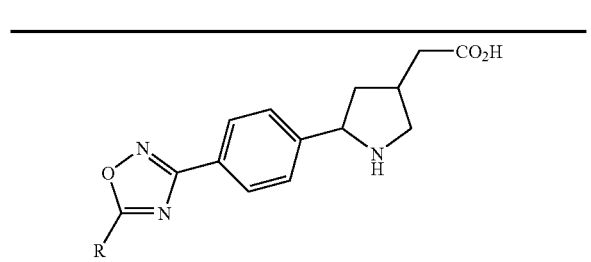

| EXAMPLE | R | LC-1 (min) | ESI-MS (M + H) |
|---|---|---|---|
| 6 | (biphenyl) | 3.4 | 426.1 |
| 7 | (F3C-CH2-phenyl) | 3.4 | 446.1 |
| 8 | (isobutyl-fluorophenyl) | 4.0 | 424.2 |
| 9 | (gem-difluorocyclopentyl-phenyl) | 3.4 | 454.1 |
| 10 | (gem-difluorocyclopentyl-phenyl) | 3.4 | 454.1 |
| 11 | (isopentyl-fluorophenyl) | 4.2 | 438.2 |
| 12 | (gem-difluorocyclohexyl-phenyl) | 3.3 | 468.2 |
| 13 | (gem-difluorocyclohexyl-phenyl) | 3.4 | 468.2 |
| 14 | (fluorocyclopentyl-phenyl) | 3.0 | 436.2 |
| 15 | (fluorocyclopentyl-phenyl) | 3.0 | 436.2 |

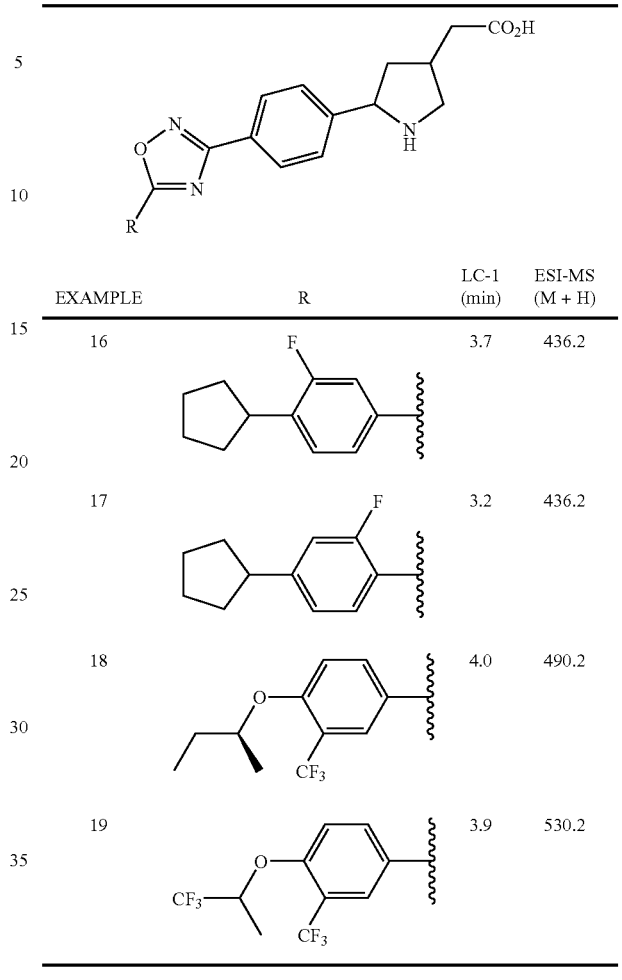

| EXAMPLE | R | LC-1 (min) | ESI-MS (M + H) |
|---|---|---|---|
| 16 | (cyclopentyl-fluorophenyl) | 3.7 | 436.2 |
| 17 | (cyclopentyl-fluorophenyl) | 3.2 | 436.2 |
| 18 | (sec-butoxy-CF3-phenyl) | 4.0 | 490.2 |
| 19 | (CF3-isopropoxy-CF3-phenyl) | 3.9 | 530.2 |

Examples 20-27

The following examples were prepared using procedures analogous to those described in EXAMPLE 5 substituting AMIDOXIME 5 for AMIDOXIME 4 and the appropriate carboxylic acids for 4-cyclopentylbenzoic acid in Step A.

| EXAMPLE | R | LC-1 (min) | ESI-MS (M + H) |
|---|---|---|---|
| 20 | (cyclopentyl-phenyl) | 3.5 | 418.2 |

-continued

| EXAMPLE | R | LC-1 (min) | ESI-MS (M + H) |
|---|---|---|---|
| 21 | 4-(2-(trifluoromethyl)...)phenyl (F₃C-CH₂-C₆H₄-) | 3.4 | 447.1 |
| 22 | 4-cyclohexylphenyl | 3.6 | 432.3 |
| 23 | 3-chloro-4-isopropoxyphenyl | 3.6 | 442.1 |
| 24 | 3-chloro-4-cyclopentyloxyphenyl | 3.7 | 468.1 |
| 25 | 3-chloro-4-isobutoxyphenyl | 3.8 | 456.1 |
| 26 | 4-(3,3-difluorocyclopentyl)phenyl | 3.7 | 454.2 |
| 27 | 4-(3,3-difluorocyclopentyl)phenyl | 3.7 | 454.1 |

Example 28

Trans-2-(4-(5-(4-cyclohexylphenyl)-1,2,4-oxadiazol-3-yl)phenyl)-4-pyrrolidineacetic acid Step A: Trans-N-tert-butyloxycarbonyl-2-(4-(5-(4-cyclohexylphenyl)-1,2,4-oxadiazol-3-yl)phenyl)-4-(2-propenyl)-pyrrolidine The title compound was prepared using a procedure analogous to that described in EXAMPLE 1 substituting AMIDOXIME 6 for AMIDOXIME 1 and 4-cyclohexylbenzoic acid for 4-(2-methylpropyl)benzoic acid, respectively, in Step A: $^1$H NMR δ 1.13-1.58 (m, 15H), 1.77-1.96 (m, 7H), 2.05-2.63 (m, 3H), 3.25 (m, 1H), 3.83 (m, 1H), 4.91-5.07 (m, 3H), 5.74 (m, 1H), 7.29 (d, J=8.0, 2H), 7.38 (d, J=8.3, 2H), 8.12 (m, 4H).

Step B: Trans-2-(4-(5-(4-cyclohexylphenyl)-1,2,4-oxadiazol-3-yl)phenyl)-4-pyrrolidineacetic acid Ruthenium(III) chloride hydrate (0.1 mg, 0.5 µmol) was added into a solution of trans-N-tert-butyloxycarbonyl-2-(4-(5-(4-cyclohexylphenyl)-1,2,4-oxadiazol-3-yl)phenyl)-4-(2-propenyl)-pyrrolidine (12 mg, 0.02 mmol) and sodium periodate (23 mg, 0.11 mmol) in a mixed solvent (7.0 mL) of 2:2:3 v/v/v CCl₄/CH₃CN/H₂O. The mixture was stirred at rt for 1 hr and then partitioned between H₂O (10 mL) and CH₂Cl₂ (10 mL). The aqueous layer was separated and extracted with CH₂Cl₂ (3×10 mL). Organic layers were combined, dried over Na₂SO₄, and concentrated to give the crude acid as a colorless syrup.

A solution of the aforementioned crude acid in 2.5 mL of 20% trifluoroacetic acid in CH₂Cl₂ was stirred at rt for 30 min. The solvent was removed and the residue was purified on HPLC: $^1$H NMR δ 1.26 (m, 2H), 1.43 (m, 4H), 1.74 (m, 2H), 1.83 (m, 4H), 2.25 (m, 1H), 2.55 (m, 4H), 2.95 (m, 1H), 3.12 (dd, J=8.0, 11.8, 1H), 3.69 (dd, J=7.7, 12.3, 1H), 4.83 (m, 1H), 7.41 (d, J=8.3, 2H), 7.60 (d, J=8.3, 2H), 8.07 (d, J=8.3, 2H), 8.18 (d, J=8.3, 2H).

Examples 29-32

The following examples were prepared using procedures analogous to those described in EXAMPLE 18 substituting the appropriate carboxylic acids for 4-cyclohexylbenzoic acid in Step A.

| EXAMPLE | R | LC-1 (min) | ESI-MS (M + H) |
|---|---|---|---|
| 29 | 4-(3,3-difluorocyclopentyl)phenyl | 3.4 | 454.1 |
| 30 | 3-fluoro-4-isopropoxyphenyl | 3.4 | 426.2 |
| 31 | 4-(3,3-difluorocyclopentyl)phenyl | 3.4 | 454.2 |
| 32 | 4-(4,4-difluorocyclohexyl)phenyl | 3.7 | 468.2 |

Example 33

Trans-2-(4-(5-(4-((1R)-3,3-difluorocyclopentyl)phenyl)-1,2,4-oxadiazol-3-yl)-3-methyl-phenyl)-4-pyrrolidineacetic acid The title compound was prepared using a procedure analogous to that described in EXAMPLE 4 substituting AMIDOXIME 7 for AMIDOXIME 3 and 4-((1R)-3,3-difluorocyclopentyl)benzoic acid for 4-(4-fluorophenyl)-5-(trifluoromethyl)thiophene-2-carboxylic acid, respectively, in Step A: $^1$H NMR δ 1.87 (m, 1H), 2.25 (m, 5H), 2.46 (m, 3H), 2.61 (m, 1H), 2.65 (s, 314), 2.96 (m, 1H), 3.12 (dd, J=7.9, 10.8, 1H), 3.41 (m, 1H), 3.71 (dd, J=7.7, 12.0, 1H), 4.81 (m, 1H), 7.40-7.50 (m, 4H), 8.10-8.12 (m, 3H).

Examples 34, 35

These examples were the diastereomers of EXAMPLE 33. The precursors of EXAMPLE 33—methyl trans-N-tert-butyloxycarbonyl-2-(4-(5-(4-((R)-3,3-difluorocyclopentyl)phenyl)-1,2,4-oxadiazol-3-yl)-3-methyl-phenyl)-4-pyrrolidineacetate—were separated on Chiralpak AD 20×250 mm column with isocratic 50:50 v/v heptane/EtOH over 50 min, flow rate at 7.0 mL/min, and UV wavelength at 254 nm. The precursor of EXAMPLE 34 has a shorter retention time under this separation condition than does that of EXAMPLE 35.

| EXAMPLE | R | LC-1 (min) | ESI-MS (M + H) |
|---|---|---|---|
| 34 | 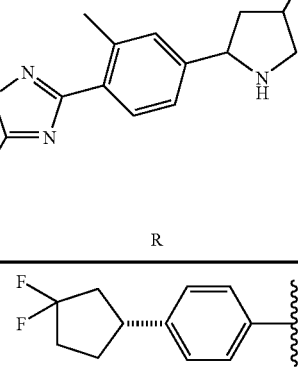 | 3.1 | 468.2 |
| 35 | 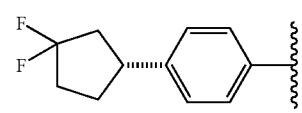 | 3.1 | 468.2 |

Biological Activity

The S1P$_1$/Edg1, S1P$_3$/Edg3, S1P$_2$/Edg5, S1P$_4$/Edg6 or S1P$_5$/Edg8 activity of the compounds of the present invention can be evaluated using the following assays:

Ligand Binding to Edg/SIP Receptors Assay $^{33}$P-sphingosine-1-phosphate was synthesized enzymatically from γ$^{33}$P-ATP and sphingosine using a crude yeast extract with sphingosine kinase activity in a reaction mix containing 50 mM KH$_2$PO$_4$, 1 mM mercaptoethanol, 1 mM Na$_3$VO$_4$, 25 mM KF, 2 mM semicarbazide, 1 mM Na$_2$EDTA, 5 mM MgCl$_2$, 50 mM sphingosine, 0.1% TritonX-114, and 1 mCi γ$^{33}$P-ATP (NEN; specific activity 3000 Ci/mmol). Reaction products were extracted with butanol and $^{33}$P-sphingosine-1-phosphate was purified by HPLC.

Cells expressing EDG/S1P receptors were harvested with enzyme-free dissociation solution (Specialty Media, Lavallette, N.J.). They were washed once in cold PBS and suspended in binding assay buffer consisting of 50 mM HEPES-Na, pH 7.5, 5 mM MgCl$_2$, 1 mM CaCl$_2$, and 0.5% fatty acid-free BSA. $^{33}$P-sphingosine-1-phosphate was sonicated with 0.1 nM sphingosine-1-phosphate in binding assay buffer; 100 μl of the ligand mixture was added to 100 μl cells (1×10$^6$ cells/ml) in a 96 well microtiter dish. Binding was performed for 60 min at room temperature with gentle mixing. Cells were then collected onto GF/B filter plates with a Packard Filtermate Universal Harvester. After drying the filter plates for 30 min, 40 μl of Microscint 20 was added to each well and binding was measured on a Wallac Microbeta Scintillation Counter. Non-specific binding was defined as the amount of radioactivity remaining in the presence of 0.5 μM cold sphingosine-1-phosphate.

Alternatively, ligand binding assays were performed on membranes prepared from cells expressing Edg/S1P receptors. Cells were harvested with enzyme-free dissociation solution and washed once in cold PBS. Cells were disrupted by homogenization in ice cold 20 mM HEPES pH 7.4, 10 mM EDTA using a Kinematica polytron (setting 5, for 10 seconds). Homogenates were centrifuged at 48,000×g for 15 min at 4° C. and the pellet was suspended in 20 mM HEPES pH 7.4, 0.1 mM EDTA. Following a second centrifugation, the final pellet was suspended in 20 mM HEPES pH 7.4, 100 mM NaCl, 10 mM MgCl$_2$. Ligand binding assays were performed as described above, using 0.5 to 2 μg of membrane protein.

Agonists and antagonists of Edg/S1P receptors can be identified in the $^{33}$P-sphingosine-1-phosphate binding assay. Compounds diluted in DMSO, methanol, or other solvent, were mixed with probe containing $^{33}$P-sphingosine-1-phosphate and binding assay buffer in microtiter dishes. Membranes prepared from cells expressing Edg/S1P receptors were added, and binding to $^{33}$P-sphingosine-1-phosphate was performed as described. Determination of the amount of binding in the presence of varying concentrations of compound and analysis of the data by non-linear regression software such as MRLCalc (Merck Research Laboratories) or PRISM (GraphPad Software) was used to measure the affinity of compounds for the receptor. Selectivity of compounds for Edg/S1P receptors was determined by measuring the level of $^{33}$P-sphingosine-1-phosphate binding in the presence of the compound using membranes prepared from cells transfected with each respective receptor (S1P$_1$/Edg1, S 1P$_3$/Edg3, S1P$_2$/Edg5, S1P$_4$/Edg6, S1P$_5$/Edg8).

$^{35}$S-GTPγS Binding Assay

Functional coupling of S1P/Edg receptors to G proteins was measured in a 35-GTPγS binding assay. Membranes prepared as described in the Ligand Binding to Edg/S1P Receptors Assay (1-10 μg of membrane protein) were incubated in a 200 μl volume containing 20 mM HEPES pH 7.4, 100 mM NaCl, 10 mM MgCl$_2$, 5 μM GDP, 0.1% fatty acid-free BSA (Sigma, catalog A8806), various concentrations of sphingosine-1-phosphate, and 125 pM $^{35}$S-GTPγS (NEN; specific activity 1250 Ci/mmol) in 96 well microtiter dishes. Binding was performed for 1 hour at room temperature with gentle mixing, and terminated by harvesting the membranes onto GF/B filter plates with a Packard Filtermate Universal Harvester. After drying the filter plates for 30 min, 40 μl of Microscint 20 was added to each well and binding was measured on a Wallac Microbeta Scintillation Counter.

Agonists and antagonists of S1P/Edg receptors can be discriminated in the $^{35}$S-GTPγS binding assay. Compounds diluted in DMSO, methanol, or other solvent, were added to microtiter dishes to provide final assay concentrations of 0.01 nM to 10 µM. Membranes prepared from cells expressing S1P/Edg receptors were added, and binding to $^{35}$S-GTPγS was performed as described. When assayed in the absence of the natural ligand or other known agonist, compounds that stimulate $^{35}$S-GTPγS binding above the endogenous level were considered agonists, while compounds that inhibit the endogenous level of $^{35}$S-GTPγS binding were considered inverse agonists. Antagonists were detected in a $^{35}$S-GTPγS binding assay in the presence of a sub-maximal level of natural ligand or known S1P/Edg receptor agonist, where the compounds reduced the level of $^{35}$S-GTPγS binding. Determination of the amount of binding in the presence of varying concentrations of compound was used to measure the potency of compounds as agonists, inverse agonists, or antagonists of S1P/Edg receptors. To evaluate agonists, percent stimulation over basal was calculated as binding in the presence of compound divided by binding in the absence of ligand, multiplied by 100. Dose response curves were plotted using a non-linear regression curve fitting program MRLCalc (Merck Research Laboratories), and $EC_{50}$ values were defined to be the concentration of agonist required to give 50% of its own maximal stimulation. Selectivity of compounds for S1P/Edg receptors was determined by measuring the level of $^{35}$S-GTPγS binding in the presence of compound using membranes prepared from cells transfected with each respective receptor.

Intracellular Calcium Flux Assay

Functional coupling of S1P/Edg receptors to G protein associated intracellular calcium mobilization was measured using FLIPR (Fluorescence Imaging Plate Reader, Molecular Devices). Cells expressing S1P/Edg receptors were harvested and washed once with assay buffer (Hanks Buffered Saline Solution (BRL) containing 20 mM HEPES, 0.1% BSA and 710 µg/ml probenicid (Sigma)). Cells were labeled in the same buffer containing 500 nM of the calcium sensitive dye Fluo-4 (Molecular Probes) for 1 hour at 37° C. and 5% $CO_2$. The cells were washed twice with buffer before plating 1.5× $10^5$ per well (90 µl) in 96 well polylysine coated black microtiter dishes. A 96-well ligand plate was prepared by diluting sphingosine-1-phosphate or other agonists into 200 µl of assay buffer to give a concentration that was 2-fold the final test concentration. The ligand plate and the cell plate were loaded into the FLIPR instrument for analysis. Plates were equilibrated to 37° C. The assay was initiated by transferring an equal volume of ligand to the cell plate and the calcium flux was recorded over a 3 min interval. Cellular response was quantitated as area (sum) or maximal peak height (max). Agonists were evaluated in the absence of natural ligand by dilution of compounds into the appropriate solvent and transfer to the Fluo-4 labeled cells. Antagonists were evaluated by pretreating Fluo-4 labeled cells with varying concentrations of compounds for 15 min prior to the initiation of calcium flux by addition of the natural ligand or other S1P/Edg receptor agonist.

Preparation of Cells Expressing S1P/Edg Receptors

Any of a variety of procedures may be used to clone $S1P_1$/Edg1, $S1P_3$/Edg3, $S1P_2$/Edg5, S $1P_4$/Edg6 or $S1P_5$/Edg8. These methods include, but are not limited to, (1) a RACE PCR cloning technique (Frohman, et al., 1988, *Proc. Natl. Acad. Sci. USA* 85: 8998-9002). 5' and/or 3' RACE may be performed to generate a full-length cDNA sequence; (2) direct functional expression of the Edg/S1P cDNA following the construction of an S1P/Edg-containing cDNA library in an appropriate expression vector system; (3) screening an S1P/Edg-containing cDNA library constructed in a bacteriophage or plasmid shuttle vector with a labeled degenerate oligonucleotide probe designed from the amino acid sequence of the S1P/Edg protein; (4) screening an SIP/Edg-containing cDNA library constructed in a bacteriophage or plasmid shuttle vector with a partial cDNA encoding the S1P/Edg protein. This partial cDNA is obtained by the specific PCR amplification of S1P/Edg DNA fragments through the design of degenerate oligonucleotide primers from the amino acid sequence known for other proteins which are related to the S1P/Edg protein; (5) screening an S1P/Edg-containing cDNA library constructed in a bacteriophage or plasmid shuttle vector with a partial cDNA or oligonucleotide with homology to a mammalian S1P/Edg protein. This strategy may also involve using gene-specific oligonucleotide primers for PCR amplification of S1P/Edg cDNA; or (6) designing 5' and 3' gene specific oligonucleotides using the S1P/Edg nucleotide sequence as a template so that either the full-length cDNA may be generated by known RACE techniques, or a portion of the coding region may be generated by these same known RACE techniques to generate and isolate a portion of the coding region to use as a probe to screen one of numerous types of cDNA and/or genomic libraries in order to isolate a full-length version of the nucleotide sequence encoding S1P/Edg.

It is readily apparent to those skilled in the art that other types of libraries, as well as libraries constructed from other cell types- or species types, may be useful for isolating an S1P/Edg-encoding DNA or an SIP/Edg homologue. Other types of libraries include, but are not limited to, cDNA libraries derived from other cells.

It is readily apparent to those skilled in the art that suitable cDNA libraries may be prepared from cells or cell lines which have S1P/Edg activity. The selection of cells or cell lines for use in preparing a cDNA library to isolate a cDNA encoding S1P/Edg may be done by first measuring cell-associated S1P/Edg activity using any known assay available for such a purpose.

Preparation of cDNA libraries can be performed by standard techniques well known in the art. Well known cDNA library construction techniques can be found for example, in Sambrook et al., 1989, *Molecular Cloning: A Laboratory Manual*; Cold Spring Harbor Laboratory, Cold Spring Harbor, N.Y. Complementary DNA libraries may also be obtained from numerous commercial sources, including but not limited to Clontech Laboratories, Inc. and Stratagene.

An expression vector containing DNA encoding an S1P/Edg-like protein may be used for expression of S1P/Edg in a recombinant host cell. Such recombinant host cells can be cultured under suitable conditions to produce S1P/Edg or a biologically equivalent form. Expression vectors may include, but are not limited to, cloning vectors, modified cloning vectors, specifically designed plasmids or viruses. Commercially available mammalian expression vectors may be suitable for recombinant S1P/Edg expression.

Recombinant host cells may be prokaryotic or eukaryotic, including but not limited to, bacteria such as *E. coli*, fungal cells such as yeast, mammalian cells including, but not limited to, cell lines of bovine, porcine, monkey and rodent origin; and insect cells including but not limited to *Drosophila* and silkworm derived cell lines.

The nucleotide sequences for the various S1P/Edg receptors are known in the art. See, for example, the following:

$S1P_1$/Edg1 Human

Hla, T. and T. Maciag 1990 An abundant transcript induced in differentiating human endothelial cells encodes a polypeptide with structural similarities to G-protein coupled receptors. J. Biol. Chem. 265:9308-9313, hereby incorporated by reference in its entirety.

WO91/15583, published on Oct. 17, 1991, hereby incorporated by reference in its entirety.

WO99/46277, published on Sep. 16, 1999, hereby incorporated by reference in its entirety.

S1P₁/Edg1 Mouse

WO0059529, published Oct. 12, 2000, hereby incorporated by reference in its entirety.

U.S. Pat. No. 6,323,333, granted Nov. 27, 2001, hereby incorporated by reference in its entirety.

S1P₁/Edg1 Rat

Lado, D. C., C. S. Browe, A. A. Gaskin, J. M. Borden, and A. J. MacLennan. 1994 Cloning of the rat edg-1 immediate-early gene: expression pattern suggests diverse functions. Gene 149: 331-336, hereby incorporated by reference in its entirety.

U.S. Pat. No. 5,585,476, granted Dec. 17, 1996, hereby incorporated by reference in its entirety.

U.S. Pat. No. 5,856,443, granted Jan. 5, 1999, hereby incorporated by reference in its entirety.

S1P₃/Edg3 Human

An, S., T. Bleu, W. Huang, O. G. Hallmark, S. R. Coughlin, E. J. Goetzl 1997 Identification of cDNAs encoding two G protein-coupled receptors for lysosphingolipids FEBS Lett. 417:279-282, hereby incorporated by reference in its entirety.

WO 99/60019, published Nov. 25, 1999, hereby incorporated by reference in its entirety.

U.S. Pat. No. 6,130,067, granted Oct. 10, 2000, hereby incorporated by reference in its entirety.

S1P₃/Edg3 Mouse

WO 01/11022, published Feb. 15, 2001, hereby incorporated by reference in its entirety.

S1P₃/Edg3 Rat

WO 01/27137, published Apr. 19, 2001, hereby incorporated by reference in its entirety.

S1P₂/Edg5 Human

An, S., Y. Zheng, T. Bleu 2000 Sphingosine 1-Phosphate-induced cell proliferation, survival, and related signaling events mediated by G Protein-coupled receptors Edg3 and Edg5. J. Biol. Chem. 275: 288-296, hereby incorporated by reference in its entirety.

WO 99/35259, published Jul. 15, 1999, hereby incorporated by reference in its entirety.

WO99/54351, published Oct. 28, 1999, hereby incorporated by reference in its entirety.

WO 00/56135, published Sep. 28, 2000, hereby incorporated by reference in its entirety.

S1P₂/Edg5 Mouse

WO 00/60056, published Oct. 12, 2000, hereby incorporated by reference in its entirety.

S1P2/Edg5 Rat

Okazaki, H., N. Ishizaka, T. Sakurai, K. Kurokawa, K. Goto, M. Kumada, Y. Takuwa 1993 Molecular cloning of a novel putative G protein-coupled receptor expressed in the cardiovascular system. Biochem. Biophys. Res. Comm. 190: 1104-1109, hereby incorporated by reference in its entirety.

MacLennan, A. J., C. S. Browe, A. A. Gaskin, D. C. Lado, G. Shaw 1994 Cloning and characterization of a putative G-protein coupled receptor potentially involved in development. Mol. Cell. Neurosci. 5: 201-209, hereby incorporated by reference in its entirety.

U.S. Pat. No. 5,585,476, granted Dec. 17, 1996, hereby incorporated by reference in its entirety.

U.S. Pat. No. 5,856,443, granted Jan. 5, 1999, hereby incorporated by reference in its entirety.

S1P₄/Edg6 Human

Graler, M. H., G. Bernhardt, M. Lipp 1998 EDG6, a novel G-protein-coupled receptor related to receptors for bioactive lysophospholipids, is specifically expressed in lymphoid tissue. Genomics 53: 164-169, hereby incorporated by reference in its entirety.

WO 98/48016, published Oct. 29, 1998, hereby incorporated by reference in its entirety.

U.S. Pat. No. 5,912,144, granted Jun. 15, 1999, hereby incorporated by reference in its entirety.

WO 98/50549, published Nov. 12, 1998, hereby incorporated by reference in its entirety.

U.S. Pat. No. 6,060,272, granted May 9, 2000, hereby incorporated by reference in its entirety.

WO 99/35106, published Jul. 15, 1999, hereby incorporated by reference in its entirety.

WO 00/15784, published Mar. 23, 2000, hereby incorporated by reference in its entirety.

WO 00/14233, published Mar. 16, 2000, hereby incorporated by reference in its entirety.

S1P₄/Edg6 Mouse

WO 00/15784, published Mar. 23, 2000, hereby incorporated by reference in its entirety.

S1P₅/Edg8 Human

Im, D.-S., J. Clemens, T. L. Macdonald, K. R. Lynch 2001 Characterization of the human and mouse sphingosine 1-phosphate receptor, S1P₅ (Edg-8): Structure-Activity relationship of sphingosine 1-phosphate receptors. Biochemistry 40:14053-14060, hereby incorporated by reference in its entirety.

WO 00/11166, published Mar. 2, 2000, hereby incorporated by reference in its entirety.

WO 00/31258, published Jun. 2, 2000, hereby incorporated by reference in its entirety.

WO 01/04139, published Jan. 18, 2001, hereby incorporated by reference in its entirety.

EP 1 090 925, published Apr. 11, 2001, hereby incorporated by reference in its entirety.

S1P₅/Eda8 Rat

Im, D.-S., C. E. Heise, N. Ancellin, B. F. O'Dowd, G.-J. Shei, R. P. Heavens, M.

R. Rigby, T. Hla, S. Mandala, G. McAllister, S. R. George, K. R. Lynch 2000 Characterization of a novel sphingosine 1-phosphate receptor, Edg-8. J. Biol. Chem. 275: 14281-14286, hereby incorporated by reference in its entirety.

WO 01/05829, published Jan. 25, 2001, hereby incorporated by reference in its entirety.

Measurement of Cardiovascular Effects

The effects of compounds of the present invention on cardiovascular parameters can be evaluated by the following procedure:

Adult male rats (approx. 350 g body weight) were instrumented with femoral arterial and venous catheters for measurement of arterial pressure and intravenous compound administration, respectively. Animals were anesthetized with Nembutal (55 mg/kg, ip). Blood pressure and heart rate were recorded on the Gould Po-Ne-Mah data acquisition system. Heart rate was derived from the arterial pulse wave. Following an acclimation period, a baseline reading was taken (approximately 20 minutes) and the data averaged. Compound was administered intravenously (either bolus injection of approximately 5 seconds or infusion of 15 minutes duration), and data were recorded every 1 minute for 60 minutes post compound administration. Data are calculated as either the peak change in heart rate or mean arterial pressure or are calculated as the area under the curve for changes in heart rate or blood pressure versus time. Data are expressed as mean±SEM. A one-tailed Student's paired t-test is used for statistical comparison to baseline values and considered significant at $p<0.05$.

The S1P effects on the rat cardiovascular system are described in Sugiyama, A., N. N. Aye, Y. Yatomi, Y. Ozaki, K. Hashimoto 2000 Effects of Sphingosine-1-Phosphate, a naturally occurring biologically active lysophospholipid, on the rat cardiovascular system. Jpn. J. Pharmacol. 82: 338-342, hereby incorporated by reference in its entirety.

Measurement of Mouse Acute Toxicity

A single mouse is dosed intravenously (tail vein) with 0.1 ml of test compound dissolved in a non-toxic vehicle and is observed for signs of toxicity. Severe signs may include death, seizure, paralysis or unconciousness. Milder signs are also noted and may include ataxia, labored breathing, ruffling or reduced activity relative to normal. Upon noting signs, the dosing solution is diluted in the same vehicle. The diluted dose is administered in the same fashion to a second mouse and is likewise observed for signs. The process is repeated until a dose is reached that produces no signs. This is considered the estimated no-effect level. An additional mouse is dosed at this level to confirm the absence of signs.

Assessment of Lymphopenia

Compounds are administered as described in Measurement of Mouse Acute Toxicity and lymphopenia is assessed in mice at three hours post dose as follows. After rendering a mouse unconscious by $CO_2$ to effect, the chest is opened, 0.5 ml of blood is withdrawn via direct cardiac puncture, blood is immediately stabilized with EDTA and hematology is evaluated using a clinical hematology autoanalyzer calibrated for performing murine differential counts (H2000, CARESIDE, Culver City Calif.). Reduction in lymphocytes by test treatment is established by comparison of hematological parameters of three mice versus three vehicle treated mice. The dose used for this evaluation is determined by tolerability using a modification of the dilution method above. For this purpose, no-effect is desirable, mild effects are acceptable and severely toxic doses are serially diluted to levels that produce only mild effects.

In Vitro Activity of Examples

The examples disclosed herein have utility as immunoregulatory agents as demonstrated by their activity as potent and selective agonists of the $S1P_1$/Edg1 receptor over the $S1PR_3$/Edg3 receptor as measured in the assays described above. In particular, the examples disclosed herein possess a selectivity for the $S1P_1$/Edg1 receptor over the $S1PR_3$/Edg3 receptor of more than 100 fold as measured by the ratio of $EC_{50}$ for the $S1P_1$/Edg1 receptor to the $EC_{50}$ for the $S1P_3$/Edg3 receptor as evaluated in the $^{35}$S-GTPγS binding assay described above and possess an $EC_{50}$ for binding to the $S1P_1$/Edg1 receptor of less than 50 nM as evaluated by the $^{35}$S-GTPγS binding assay described above.

What is claimed is:

1. A compound represented by Formula I

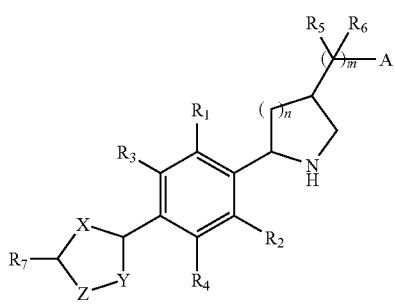

or a pharmaceutically acceptable salt thereof, wherein:
n is 0, 1, or 2;
m is 0, 1, or 2, such that when m is 0 then A is bonded directly to the azetidine (n=0), pyrrolidine (n=1), or piperidine (n=2) group shown in Formula I;

$R^1$, $R^2$, $R^3$, and $R^4$ are independently selected from the group consisting of: —H, —F, $C_1$-$C_4$alkyl, $C_1$-$C_4$perfluoroalkyl, —Cl, —Br, $C_1$-$C_8$alkoxy, and —OCF$_3$;

$R^5$ and $R^6$ are independently selected from: —H, —OH, —F, $C_1$-$C_4$ alkyl, and $C_1$-$C_4$perfluoroalkyl;

$R^7$ is selected from the group consisting of: phenyl, pyridinyl, pyrimidinyl, pyrazinyl, pyridizinyl and thienyl, each optionally substituted with one to three substituents independently selected from the group consisting of: —F, —Cl, —Br, —I, —CN, —OH, —NR$^8$R$^9$, —NO$_2$, phenyl, $C_1$-$C_6$alkyl, $C_3$-$C_6$cycloalkyl, $C_2$-$C_6$alkenyl, $C_2$-$C_6$alkynyl, $C_1$-$C_6$alkoxy, $C_3$-$C_6$cycloalkoxy, $C_1$-$C_6$alkylthio and $C_2$-$C_6$acyloxy, wherein said phenyl, $C_1$-$C_6$alkyl, $C_3$-$C_6$cycloalkyl, $C_2$-$C_6$alkenyl, $C_2$-$C_6$alkynyl, $C_1$-$C_6$alkoxy, $C_3$-$C_6$cycloalkoxy, $C_1$-$C_6$alkylthio and $C_1$-$C_6$acyloxy are each optionally substituted with one to three substituents independently selected from the group consisting of: —F, —Cl, —Br, —I, —OH and $C_1$-$C_5$alkoxy;

$R^8$ and $R^9$ are independently selected from the group consisting of: $C_1$-$C_6$ alkyl, $C_1$-$C_6$ alkenyl and $C_1$-$C_6$ alkynyl, each optionally substituted with one to three substituents independently selected from the group consisting of: —F, —Cl, —Br, —I, —OH and $C_1$-$C_5$alkoxy, or $R^8$ and $R^9$ may be joined together with the nitrogen atom to which they are attached to form a saturated monocyclic ring of 3 to 8 atoms, optionally containing 1 or 2 oxygen atoms, said ring is optionally substituted with one to three substituents independently selected from the group consisting of: —F, —Cl, —Br, —I, —OH and $C_{1-5}$alkoxy;

X, Y, and Z are independently selected from the group consisting of: —C=, —CH—, —O—, —N=, —NH—, —N(R$^{10}$)— and —S— such that the resulting ring is an aromatic heterocycle;

$R^{10}$ is selected from the group consisting of: $C_1$-$C_6$ alkyl, $C_1$-$C_6$ alkenyl and $C_1$-$C_6$ alkynyl, each optionally substituted with one to three substituents independently selected from the group consisting of: —F, —Cl, —Br, —I, —OH and $C_1$-$C_5$alkoxy;

A is selected from the group consisting of: —CO$_2$H, —PO$_3$H$_2$, —PO$_2$H$_2$, —SO$_3$H, —CONHSO$_2$R$^{11}$, —PO(R$^{11}$)OH,

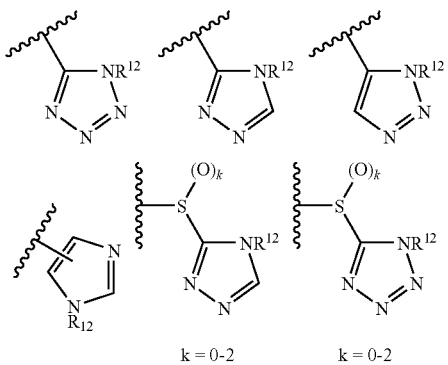

k = 0-2    k = 0-2

-continued

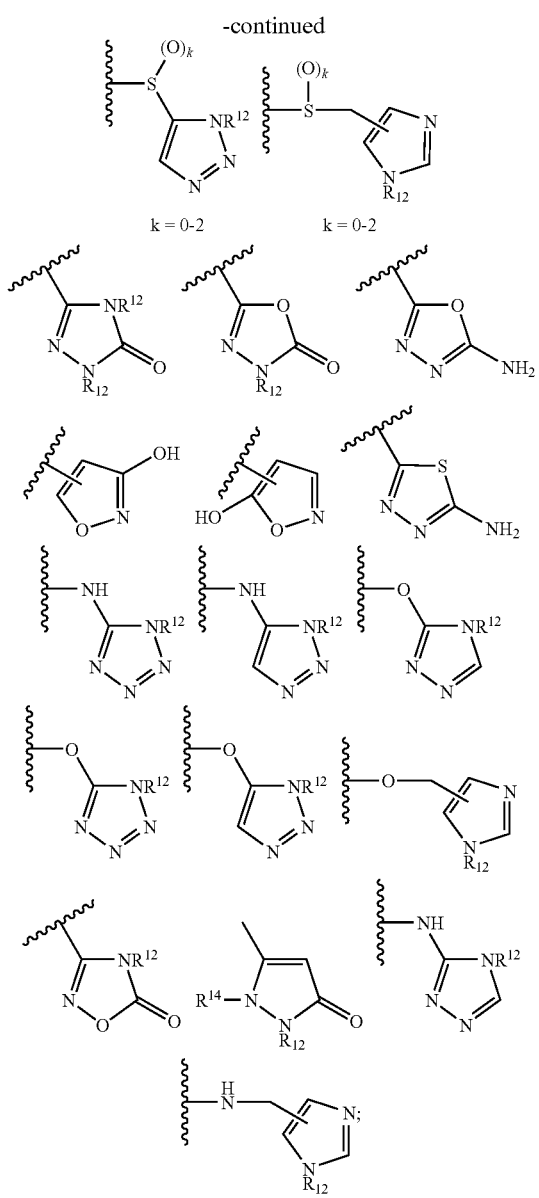

R[11] is selected from the group consisting of: $C_1$-$C_4$ alkyl, phenyl, —$CH_2OH$ and $CH(OH)$-phenyl; and
each R[12] is independently selected from the group consisting of: —H and —$CH_3$.

2. The compound according to claim 1 wherein A is —$CO_2H$.

3. The compound according to claim 1 wherein n is 1.

4. The compound according to claim 1 wherein m is 1.

5. The compound according to claim 1 wherein X is —N═, Y is —N═ and Z is —O— such that the resulting ring formed is 1,2,4-oxadiazole.

6. The compound according to claim 1 wherein R[7] is phenyl, optionally substituted with one to three substituents independently selected from the group consisting of: —F, —Cl, —Br, —I, —CN, —OH, —NR[7]R[8], —NO$_2$, phenyl, $C_1$-$C_6$alkyl, $C_3$-$C_6$cycloalkyl, $C_2$-$C_6$alkenyl, $C_2$-$C_6$alkynyl, $C_1$-$C_6$alkoxy, $C_3$-$C_6$cycloalkoxy, $C_1$-$C_6$alkylthio and $C_2$-$C_6$acyloxy, wherein said phenyl, $C_1$-$C_6$alkyl, $C_3$-$C_6$cycloalkyl, $C_2$-$C_6$alkenyl, $C_2$-$C_6$alkynyl, $C_1$-$C_6$alkoxy, $C_3$-$C_6$cycloalkoxy, $C_1$-$C_6$alkylthio and $C_1$-$C_6$acyloxy are each optionally substituted with one to three substituents independently selected from the group consisting of: —F, —Cl, —Br, —I, —OH and $C_1$-$C_5$alkoxy.

7. A compound in accordance with claim 1 represented by Formula Ia

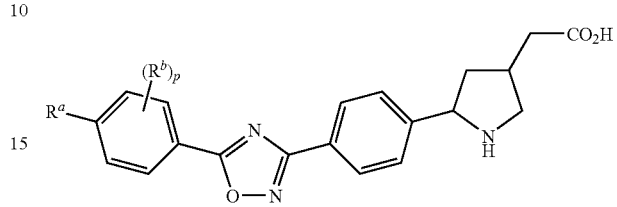

or a pharmaceutically acceptable salt thereof, wherein:
p is 0, 1 or 2;
R[a] is selected from the group consisting of: phenyl, $C_1$-$C_6$alkyl, $C_3$-$C_6$cycloalkyl, $C_1$-$C_6$ alkoxy and $C_3$-$C_6$cycloalkoxy, wherein said phenyl, $C_1$-$C_6$alkyl, $C_3$-$C_6$cycloalkyl, $C_1$-$C_6$alkoxy and $C_3$-$C_6$cycloalkoxy are each optionally substituted with one to three substituents independently selected from the group consisting of: —F, —Cl, —Br, —I and —OH; and
R[b] is selected from the group consisting of: —F, —Cl, —Br, —I, —CN, —$CH_3$, —$OCH_3$, —$CF_3$, ethynyl, —$NO_2$ and —$NH_2$.

8. The compound according to claim 7, wherein p is 0 or 1, and R[b] is selected from the group consisting of: —F, —Cl and —$CF_3$.

9. The compound according to claim 8, wherein R[a] is selected from the group consisting of: $C_3$-$C_5$alkyl, cyclopentyl, cyclohexyl, $C_2$-$C_4$alkoxy, cyclopentyloxy and cyclohexyloxy, each optionally substituted with one to three fluoro groups.

10. A mixture of stereoisomers, or a single stereoisomer in substantially pure form free of other stereoisomers, of a compound selected from the following table:

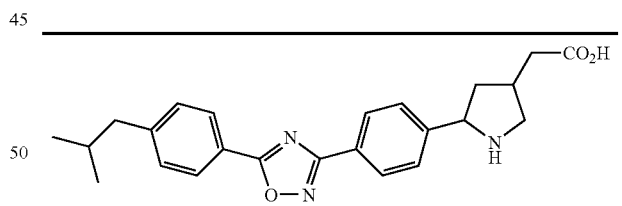

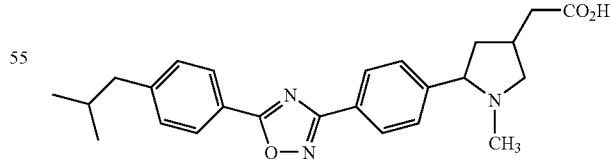

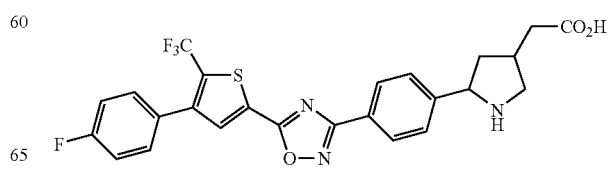

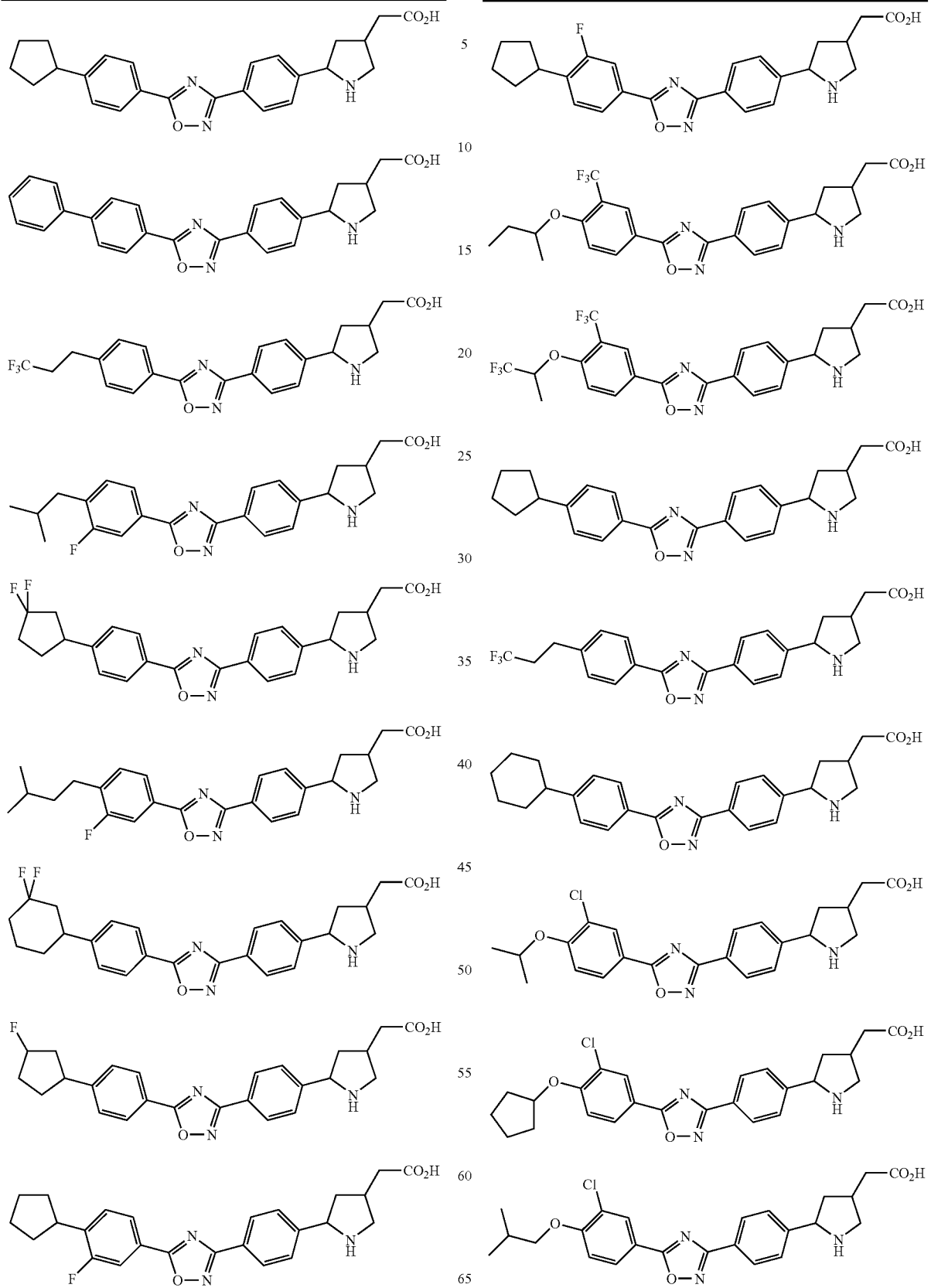

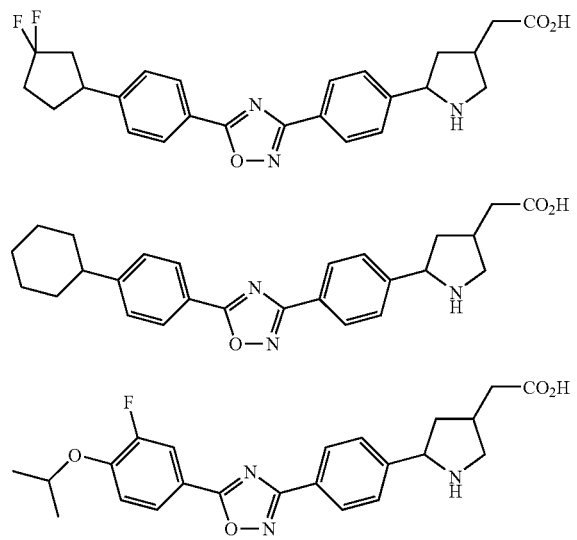
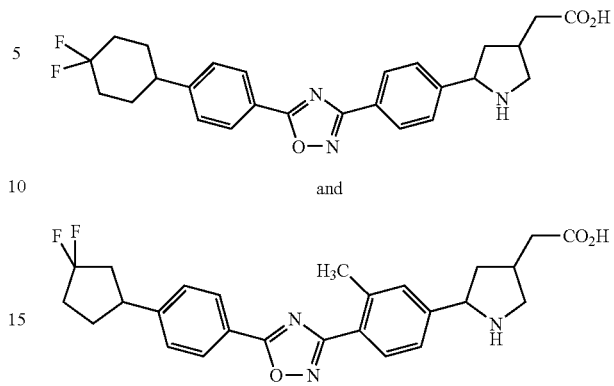
or a pharmaceutically acceptable salt of any of the above.
11. A pharmaceutical composition comprised of a compound in accordance with claim 1 in combination with a pharmaceutically acceptable carrier.
* * * * *